US008637084B2

(12) United States Patent
Yasutake et al.

(10) Patent No.: US 8,637,084 B2
(45) Date of Patent: Jan. 28, 2014

(54) TREATMENT METHOD FOR EPITHELIAL CANCEROUS ORGANISM

(75) Inventors: Mikitomo Yasutake, Tokyo (JP); Kasumi Ninomiya, Tokyo (JP); Junichi Honda, Tokyo (JP); Atsushi Ochiai, Chiba (JP); Chisako Yamauchi, Chiba (JP)

(73) Assignees: Asahi Kasei Medical Co., Ltd., Tokyo (JP); National Cancer Center, Tokyo (JP)

( * ) Notice: Subject to any disclaimer, the term of this patent is extended or adjusted under 35 U.S.C. 154(b) by 205 days.

(21) Appl. No.: 12/835,010

(22) Filed: Jul. 13, 2010

(65) Prior Publication Data

US 2011/0091471 A1 Apr. 21, 2011

Related U.S. Application Data

(60) Provisional application No. 61/247,002, filed on Sep. 30, 2009.

(30) Foreign Application Priority Data

Jul. 14, 2009 (JP) .................................. 2009-165458
Aug. 31, 2009 (JP) .................................. 2009-200410

(51) Int. Cl.
A61K 35/28 (2006.01)
A01N 25/00 (2006.01)

(52) U.S. Cl.
USPC .......................................... 424/577; 514/885

(58) Field of Classification Search
None
See application file for complete search history.

(56) References Cited

U.S. PATENT DOCUMENTS

| 2005/0191342 | A1 | 9/2005 | Tam et al. |
| 2005/0287543 | A1 | 12/2005 | Yu et al. |
| 2008/0102069 | A1 | 5/2008 | Friess et al. |
| 2011/0150868 | A1 | 6/2011 | Yu et al. |
| 2012/0039875 | A1 | 2/2012 | Yu et al. |

FOREIGN PATENT DOCUMENTS

| WO | 2005/034979 A2 | 4/2005 |
| WO | 2005/044091 A2 | 5/2005 |
| WO | 2008/031531 A1 | 3/2008 |

OTHER PUBLICATIONS

Mestas et al., J. of Immunology, 2004, 172, pp. 2731-238.*
Laurence et al (Nature Immunol, 2007, v.9, pp. 903-905.*
Feldman et al., Transplant. Proc. 1998, 30, 4126-4127.*
Lebbink et al., "Non-MHC Ligands for Inhibitory Immune Receptors: Novel Insights and Implications for Immune Regulation" *Mol. Immunol.*, vol. 44, No. 9, pp. 2153-2164, 2007.
Colonna, "Cytolytic Responses: Cadherins Put Out the Fire" *J. Exp. Med.*, vol. 203, No. 2, pp. 261-264, 2006.
Ito et al., "Killer Cell Lectin-Like Receptor G1 Binds Three Members of the Classical Cadherin Family to Inhibit NK Cell Cytotoxicity" *J. Exp. Med.*, vol. 203, No. 2, pp. 289-295, 2006.
Voehringer et al., "Lack of Proliferative Capacity of Human Effector and Memory T Cells Expressing Killer Cell Lectinlike Receptor G1 (KLRG1)" *Blood*, vol. 100, No. 10, pp. 3698-3702, 2002.
International Search Report (in Japanese and English), mailed Oct. 12, 2010, and Written Opinion and Invitation to Pay Additional Fees (in Japanese) for PCT/JP2010/061860.
Pinkas-Kramarski et al. "ErbB Receptors and EGF-like Ligands: Cell Lineage Determination and Oncogenesis Through Combinatorial Signaling," *Journal of Mammary Gland Biology and Neoplasia*, vol. 2, No. 2, pp. 97-107, 1997.
Schechter et al., "The *neu* Oncogene: An *erb-B*-Related Gene Encoding a 185, 000-$M_r$, tumour antigen," *Nature*, vol. 312, pp. 513-516, 1984.
Hudziak et al., "p185$^{HER2}$ Monoclonal Antibody has Antiproliferative Effects In Vitro and Sensitizes Human Breast Tumor Cells to Tumor Necrosis Factor," *Molecular and Cellular Biology*, vol. 9, No. 3, pp. 1165-1172, 1989.
Piccart-Gebhart et al., "Trastuzumab after Adjuvant Chemotheraphy in HER2-Positive Breast Cancer," *The New England Journal of Medicine*, vol. 353, No. 16, pp. 1659-1672, 2005.
Clynes et al., "Inhibitory Fc Receptors Modulate In Vivo Cytoxicity Against Tumor Targets," *Nature Medicine*, vol. 6, No. 4, pp. 443-446, 2000.
Izumi et al., "Tumour Biology: Herceptin Acts as an Anti-Angiogenic Cocktail," *Nature*, vol. 416, pp. 279-280, 2002.
Gennari et al., "Pilot Study of the Mechanism of Action of Preoperative Trastuzumab in Patients with Primary Operable Breast Tumors Overexpressing HER2," *Cinical Cancer Research*, vol. 10, pp. 5650-5655, 2004.
Barok et al., "Trastuzumab Causes Antibody-Dependent Cellular Cytotoxicity-Mediated Growth Inhibition of Submacroscopic JIMT-1 Breast Cancer Xenografts Despite Intrinsic Drug Resistance," *Molecular Cancer Therapeutics*, vol. 6, No. 7, pp. 2065-2072, 2007.

(Continued)

*Primary Examiner* — Michail Belyavskyi
(74) *Attorney, Agent, or Firm* — Greenblum & Bernstein, P.L.C.

(57) ABSTRACT

It is an object of the present invention to provide a novel method for decreasing the number of clinical cases for which trastuzumab administration is ineffective. The present invention provides a method for treating a living individual with epithelial cancer comprising: step (a) of selectively reducing KLRG1-positive immunocytes in the peripheral blood of a living individual with epithelial cancer ex vivo, which is positive for a cancer-specific membrane antigen expressed in epithelial cancer cells and positive for a KLRG1 ligand; and step (b) of administering, to the living individual, a therapeutic agent for cancer comprising an antibody reacting with the cancer-specific membrane antigen expressed in epithelial cancer cells and having antibody-dependent cell cytotoxicity.

19 Claims, 10 Drawing Sheets

(56) References Cited

OTHER PUBLICATIONS

Soto et al., "A Monoclonal Antibody that Inhibits Secretion from Rat Basophilic Leukemia Cells and Binds to a Novel Membrane Component," *The Journal of Immunology*, vol. 141, No. 12., pp. 4324-4332, 1988.

Abramson et al., "An Unusual Inhibitory Receptor—The Mast Cell Function-Associated Antigen (MAFA)," *Molecular Immunology*, vol. 38, pp. 1307-1313, 2002.

Hanke et al., "2F1 Antigen, The Mouse Homolog of the Rat "Mast Cell Function-Associated Antigen", is a Lectin-Like Type II Transmembrane Receptor Expressed by Natural Killer Cells," *Eur. J. Irnmunol.*, vol. 28, pp. 4409-4417, 1998.

Butcher et al., "MAFA-L, an ITIM-Containing Receptor Encoded by the Human NK Cell Gene Complex and Expressed by Basophils and NK cells," *Eur. J. Immunol.*, vol. 28, pp. 3755-3762, 1998.

Blaser et al., "Virus-Activated CD8 T Cells and Lymphokine-Activated NK Cells Express the Mast Cell Function-Associated Antigen, An Inhibitory C-type Lectin," *The Journal of Immunology*, vol. 161, No. 12, pp. 6451-6454, 1998.

Extended European Search Report issued for EP Patent App. No. 10799845.2, dated Jan. 3, 2013.

Sliwkowski et al., "Nonclinical Studies Addressing the Mechanism of Action of Trastuzumab (Herceptin)" *Seminars in Oncology*, vol. 26, No. 4, Suppl. 12, pp. 60-70, 1999.

Green et al., "Disruption of Cell-Cell Adhesion Enhances Antibody-Dependent Cellular Cytotoxicity: Implications for Antibody-Based Therapeutics of Cancer" *Cancer Research*, vol. 62, No. 23, pp. 6891-6900, 2002.

Schwartzkopff et al., "Tumor-Associated E-Cadherin Mutations Affect Binding to the Killer Cell Lectin-Like Receptor G1 in Humans" *The Journal of Immunology*, vol. 179, No. 2, pp. 1022-1029, 2007.

Wang et al., "Systemic Hypoxia Affects Exercise-Mediated Antitumor Cytotoxicity of Natural Killer Cells" *Journal of Applied Physiology*, vol. 107, No. 6, pp. 1817-1824, 2009.

Yamauchi et al., "E-Cadherin Expression on Human Carcinoma Cell Affects Trastuzumab-Mediated Antibody-Dependent Cellular Cytotoxicity Through Killer Cell Lectin-Like Receptor G1 on Natural Killer Cells" *International Journal of Cancer*, vol. 128, No. 9, pp. 2125-2137, 2011.

* cited by examiner

TREATMENT METHOD FOR EPITHELIAL CANCEROUS ORGANISM

TECHNICAL FIELD

The present invention relates to a method for treating a living individual with epithelial cancer.

BACKGROUND ART

In recent years, the number of patients who have been afflicted with and died of breast cancer is increasing at a significant level in Japan. Non-surgical therapeutic techniques for treating breast cancer were likely to be determined depending on estrogen receptor (ER) and progesterone receptor (PgR) expression conditions in the past. Drug therapy, such as hormonal therapy or anticancer drug therapy, is useful, and the response rate and viability have been improved. However, approximately 50% of human epidermal growth factor receptor-related 2 (HER2)-positive breast cancer cases have been hormone receptor-negative, and such cases have not been the targets of hormonal therapy. In recent years, molecular-targeted techniques, such as a trastuzumab-based antibody therapy against HER2-positive breast cancer, have been employed, the usefulness thereof has been demonstrated, and such techniques are expected as leading therapeutic methods in the future.

Breast cancer cells express a variety of growth factors and receptors thereof and form signal transduction systems associated with growth. An example thereof is the HER2 cancer gene that was identified in 1984, which is a member of the human epidermal growth factor receptor (EGFR, HER) family. A receptor is transmembrane glycoprotein which is classified as HER1, HER2, HER3, or HER4 based on structural similarities (Non-patent document 1). It is considered that the EGF receptor family contributes to signal transduction via dimer formation, and a receptor to which a ligand has bound forms a dimer with another receptor, thereby contributing to signal transduction.

HER2/neu, which defines the HER2 receptor, is considered to be a proto-oncogene, and it is present in chromosome 17 (17q21.1) (Non-patent document 2). Amplification and overexpression of the HER2/neu gene are observed in a variety of cancers, such as ovarian cancer, lung cancer, and gastric cancer, as well as in breast cancer. HER2-positive breast cancer accounts for 20% to 30% of all breast cancer cases. The expression level of this gene in adult normal tissue is very low. The natural course is specific, and recurrence takes place at an early stage when the patient would not undergo systemic treatment. Since the correlation of HER2 amplification with a poor prognosis of breast cancer was reported in 1987, a poor clinical course for HER2-positive metastatic breast cancer has been demonstrated by much research.

In 1986, it was reported that the anti-HER2 monoclonal antibody would inhibit malignant traits of neu transformed cells, which led to the development of trastuzumab targeting HER2. An mu4D5 mouse monoclonal antibody reacting with an extracellular domain of the HER2 receptor, which is a prototype of trastuzumab, exhibits activity of inhibiting growth of HER2-positive tumor cells in vitro (Non-patent document 3). Also, the antibody-dependent cell cytotoxicity (ADCC) of mouse splenic cells against SKBR3, which is a HER2-positive human breast cancer cell line, is reinforced by the mouse monoclonal antibody, and it is reported that ADCC activity also contributes to anti-tumor effects in vivo (Non-patent document 4). If a mouse antibody is subjected to clinical applications without modification, the problem of appearance of the human anti-mouse antibody (HAMA) arises. Thus, trastuzumab (trade name: Herceptin®) was prepared as a humanized antibody by transplanting only the variable region of an antigen-binding site of the mouse monoclonal antibody reacting with the extracellular domain of the HER2 receptor into the constant region of human IgG1.

HER2 excites a variety of signal transduction pathway networks including PI3K and MAPK. It is considered that trastuzumab binds to the HER2 receptor to inhibit such signal transduction pathway and it induces termination of a cell cycle, apoptosis, inhibition of angiogenesis, and the like to directly inhibit tumor cell growth. Also, inhibition of the Src tyrosine kinase, activation of PTEN involved therewith, and dephosphorylation of Akt have been reported. Further, it has been demonstrated that the Fc receptor that is expressed in immunocytes, including the NK cells, binds to the Fc region of trastuzumab, which has bound to the tumor cells, to exhibit the effects of killing tumor cells (ADCC activity) (Non-patent documents 5 to 8). Such effects of direct inhibition of tumor cell growth and ADCC activity are considered to be the main mechanisms of trastuzumab.

Trastuzumab targets HER2, and the therapeutic effects thereof significantly vary depending on HER2 protein expression level. It is known that the positive ratio significantly varies depending on assay technique and materials used. In order to inspect HER2 protein overexpression and DNA amplification, the immunohistochemical (IHC) method and fluorescence in situ hybridization (FISH) are extensively employed. Also, trastuzumab has been found to be very effective for postoperative adjuvant therapy involving a plurality of large-scale clinical testings, including the HERA test.

Based on a variety of studies that have been heretofore conducted, HER2 inhibition via trastuzumab administration was found to significantly influence the natural course of breast cancer. However, it has also been found that trastuzumab would not alter the entire natural course of HER2-overexpressing breast cancer, and it is said that the number of cases in which patients react with the first administration of trastuzumab alone is approximately one-third or lower than that for HER2-overexpressing breast cancer. In the case of microscopic metastatic cancer, similarly, it is suggested that a considerable percentage of tumors are tolerant to trastuzumab. However, the mechanism of trastuzumab tolerance has not been clearly elucidated. At present, the following possibilities are suggested as the mechanisms of trastuzumab tolerance: (1) insufficient inhibition of the HER2 extracellular region due to insufficient accession of trastuzumab; (2) a lowered HER2 expression level; (3) an altered HER2 regulator located downstream (e.g., lowered $p27^{kip1}$ and quenching or inactivation of PTEN); (4) the occurrence of signal transmission by an alternate pathway (overexpression of the insulin-like growth factor I receptor (IGF1R)); and (5) lowered immunity (lowered ADCC activity, in particular).

The tolerance mechanism related to immunity of (5) above has not been actively examined. In recent years, the functions of the NK cell, which is a factor associated with ADCC activity as a main action mechanism of trastuzumab, have become elucidated. Inhibitory receptors are expressed in NK cells, and the killer cell lectin-like receptor G1 (KLRG1) was identified as one such inhibitory receptor. Most of the ligands of inhibitory receptors that have been found with regard to NK cells were associated with the MHC class I molecule. In 2006, M. Ito et al. reported that the KLRG1 ligand was not of the MHC class I molecule.

KLRG1 was discovered as a functional molecule expressed in the RBL-2H3 rat basophilic leukemia cell line (MAFA: the mast cell function-associated antigen) (Non-patent document 9). KLRG1 crosslinks with the anti-KLRG1 antibody in the RBL-2H3 cell, and the degranulation reaction caused by Fc receptor stimulation is inhibited. As a result of cDNA cloning of rat KLRG1, it has been reported by Pecht et al. that KLRG1 is a homodimer of the type II transmembrane protein having a C-type lectin-like structure in the extracellular region and an immunoreceptor tyrosine-based inhibitory motif (ITIM) in the intracellular region (Non-patent document 10). KLRG1 is expressed in some NK or T cells in the case of humans and mice (Non-patent documents 11 to 13). In contrast, it is known that expression thereof is observed in approximately 50% of the peripheral blood NK cells of healthy individuals.

PRIOR ART REFERENCES

Non-Patent Documents

[Non-patent document 1] Pinkas-Kramarsld, R., I. Arloy and Y. Yarden (1997) ErbB receptors and EGF-like ligands: cell lineage determination and oncogenesis through combinatorial signaling. J Mammary Gland Biol Neoplasia, 2:97-107.

[Non-patent document 2] Schechter, A. L., D. F. Stem, L. Vaidyanathan, S. J. Decker, J. A. Drebin, M. I. Greene and R. A. Weinberg (1984) The neu oncogene: an erb-B-related gene encoding a 185,000-Mr tumour antigen. Nature, 312: 513-516.

[Non-patent document 3] Hudziak R M, Lewis G D, Winget M, Fendly B M, Shepard H M, Ullrich A (1989) p185HER2 monoclonal antibody has antiproliferative effects in vitro and sensitizes human breast tumor cells to tumor necrosis factor. Mol Cell Biol, 9(3):1165-72.

[Non-patent document 4] Piccart-Gebhart M J, Procter M, Leyland-Jones B, Goldhirsch A, Untch M, Smith I, Gianni L, Baselga J, Bell R, Jackisch C, Cameron D, Dowsett M, Barrios C H, Steger Huang C S, Andersson M, Inbar M, Lichinitser M, Láng I, Nitz U, Iwata H, Thomssen C, Lohrisch C, Suter T M, Rüschoff J, Suto T, Greatorex V, Ward C, Straehle C, McFadden E, Dolci M S, Gelber R D; Herceptin Adjuvant (HERA) Trial Study Team (2005) Trastuzumab after adjuvant chemotherapy in HER2-positive breast cancer. N Engl J Med, 353(16):1659-72

[Non-patent document 5] Clynes R A, Towers T L, Presta L G, Ravetch J V (2000) Inhibitory Fc receptors modulate in vivo cytoxicity against tumor targets. Nat Med, 6(4):443-6.

[Non-patent document 6] Izumi Y, Xu L, di Tomaso E, Fukumura D, Jain R K (2002) Tumour biology: herceptin acts as an anti-angiogenic cocktail. Nature, 416(6878):279-80

[Non-patent document 7] Gennari R, Menard S, Fagnoni F, Ponchio L, Scelsi M, Tagliabue E, Castiglioni F, Villani L, Magalotti C, Gibelli N, Oliviero B, Ballardini B, Da Prada G, Zambelli A, Costa A (2004) Pilot study of the mechanism of action of preoperative trastuzumab in patients with primary operable breast tumors overexpressing HER2. Clin Cancer Res., 10(17):5650-5

[Non-patent document 8] Barok, et al., (2007) Trastuzumab causes antibody-dependent cellular cytotoxicity-mediated growth inhibition of submacroscopic JIMT-1 breast cancer xenografts despite intrinsic drug resistance. Molecular Cancer Therapeutics, 6:2065-2072.

[Non-patent document 9] Ortega Soto E, Pecht I (1988) A monoclonal antibody that inhibits secretion from rat basophilic leukemia cells and binds to a novel membrane component. J Immunol, 141(12):4324-32.

[Non-patent document 10] Abramson J, Xu R, Pecht I (2002) An unusual inhibitory receptor—the mast cell function-associated antigen (MAFA). Mol Immunol, 38(16-18): 1307-13.

[Non-patent document 11] Hanke T, Corral L, Vance R E, Raulet D H (1998) 2F1 antigen, the mouse homolog of the rat "mast cell function-associated antigen", is a lectin-like type II transmembrane receptor expressed by natural killer cells. Eur J. Immunol., 28(12):4409-17

[Non-patent document 12] Butcher S, Arney K L, Cook G P (1998) MAFA-L, an ITIM-containing receptor encoded by the human NK cell gene complex and expressed by basophils and NK cells. Eur J. Immunol., 28(11):3755-62

[Non-patent document 13] Blaser C, Kaufmann M, Pircher H (1998) Virus-activated CD8 T cells and lymphokine-activated NK cells express the mast cell function-associated antigen, an inhibitory C-type lectin. J. Immunol., 161(12): 6451-4

SUMMARY OF THE INVENTION

Object to be Attained by the Invention

Application of trastuzumab therapy is expanding from recurrence therapy to postoperative adjuvant therapy for the purpose of recurrence prevention and preoperative therapy. Further improvement in curability of HER2-positive cases is expected. Since the application range is expanded, it is expected that targets of trastuzumab administration is significantly increased. At present, however, there are many groups for which trastuzumab administration is ineffective among target cases. It is accordingly an object of the present invention to provide a novel method for decreasing the number of clinical cases for which trastuzumab administration is ineffective.

Means for Attaining the Object

The present inventors have conducted concentrated studies in order to attain the above object. As a result, they discovered that selective reduction of KLRG1-positive immunocytes from the peripheral blood of a living individual at the time of administration of the anti-HER2 monoclonal antibody (i.e., trastuzumab) would realize exertion of anti-cancer effects in a living individual for which administration of the anti-HER2 monoclonal antibody had been ineffective in the past. This has led to the completion of the present invention. Specifically, the present invention provides the following.

[1] A method for treating a living individual with epithelial cancer comprising:

step (a) of selectively reducing KLRG1-positive immunocytes in the peripheral blood of a living individual with epithelial cancer ex vivo, which is positive for a cancer-specific membrane antigen expressed in epithelial cancer cells and positive for a KLRG1 ligand; and step (b) of administering, to the living individual, a therapeutic agent for cancer comprising an antibody reacting with the cancer-specific membrane antigen expressed in epithelial cancer cells and having antibody-dependent cell cytotoxicity.

[2] The method according to [1], wherein step (a) comprises extracorporeally circulating the peripheral blood of a living individual and allowing the same to pass through a cell adsorbers having higher affinity for KLRG1-positive immunocytes than for KLRG1-negative immunocytes to selectively reduce KLRG1-positive immunocytes.

[3] The method according to [1], wherein administration of a therapeutic agent for cancer of step (b) is carried out during or after step (a) of selectively reducing the KLRG1-positive immunocytes in the peripheral blood of a living individual ex vivo.

[4] The method according to [1], wherein step (a) and step (b) are each carried out a plurality of times as a set of steps and all the procedures for administration of therapeutic agents for cancer in step (b) are carried out between the first and the last implementations of step (a) of selectively reducing the KLRG1-positive immunocytes in the peripheral blood of the living individual ex vivo or after the last implementation.

[5] The method according to [1], wherein the cancer-specific membrane antigen expressed in epithelial cancer cells is HER2.

[6] The method according to [5], wherein an antibody reacting with the cancer-specific membrane antigen expressed in epithelial cancer cells is trastuzumab.

[7] The method according to [1], wherein the cancer-specific membrane antigen expressed in epithelial cancer cells is CEA.

[8] The method according to [1], wherein the KLRG1-positive immunocytes are KLRG1-positive NK cells.

[9] The method according to [1], wherein the KLRG1 ligand is selected from the group consisting of E-cadherin, N-cadherin, R-cadherin, and a fragment of any thereof.

[10] The method according to any of [1] to [9], wherein the epithelial cancer is breast cancer.

[11] The method according to any of [1] to [9], wherein the epithelial cancer is gastric cancer.

[12] The method according to [2], wherein the cell adsorber having higher affinity for KLRG1-positive immunocytes than for KLRG1-negative immunocytes comprises a water-insoluble carrier on which a substance having affinity for KLRG1 is immobilized.

[13] The method according to [12], wherein the substance having affinity for KLRG1 is an antibody reacting with KLRG1.

[14] The method according to [12], wherein the substance having affinity for KLRG1 is E-cadherin.

[15] The method according to any of [12] to [14], wherein the water-insoluble carrier is magnetic particles.

[16] The method according to any of [12] to [14], wherein the water-insoluble carrier is a nonwoven fabric.

[17] A method for treating a living individual with epithelial cancer comprising:
step (a) of selectively reducing the KLRG1-positive immunocytes in the peripheral blood of a living individual with epithelial cancer, which is positive for the cancer-specific membrane antigen expressed in epithelial cancer cells and positive for a KLRG1 ligand, ex vivo with the use of the cell adsorbers having higher affinity for KLRG1-positive immunocytes than for KLRG1-negative immunocytes; and
step (b) of administering, to the living individual, a therapeutic agent for cancer comprising an antibody reacting with the cancer-specific membrane antigen expressed in epithelial cancer cells and having antibody-dependent cell cytotoxicity.

Further, the present invention provides a method for reinforcing antibody-dependent cell cytotoxicity of a cancer cell-damaging agent comprising bringing the cancer cell-damaging agent comprising an antibody reacting with the cancer-specific membrane antigen expressed in epithelial cancer cells and having antibody-dependent cell cytotoxicity into contact with mononuclear cells in which the KLRG1-positive immunocytes had been selectively reduced and epithelial cancer cells that are positive for the cancer-specific membrane antigen and positive for the KLRG1 ligand.

Further, the present invention provides the use of mononuclear cells in which the KLRG1-positive immunocytes had been selectively reduced, for reinforcement of the antibody-dependent cell cytotoxicity of an antibody reacting with the cancer-specific membrane antigen against epithelial cancer cells, which are positive for the cancer-specific membrane antigen expressed in epithelial cancer cells and positive for the KLRG1 ligand, which comprises bringing an antibody reacting with the cancer-specific membrane antigen expressed in epithelial cancer cells into contact with mononuclear cells in which the KLRG1-positive immunocytes had been selectively reduced and with the epithelial cancer cells.

EFFECTS OF THE INVENTION

According to the present invention, effective anti-cancer effects can be attained even in a living individual in which anti-cancer effects could not be attained in the past through administration of an antibody reacting with the cancer-specific membrane antigen expressed in epithelial cancer cells.

EMBODIMENTS FOR CARRYING OUT THE INVENTION

Figure 1A:
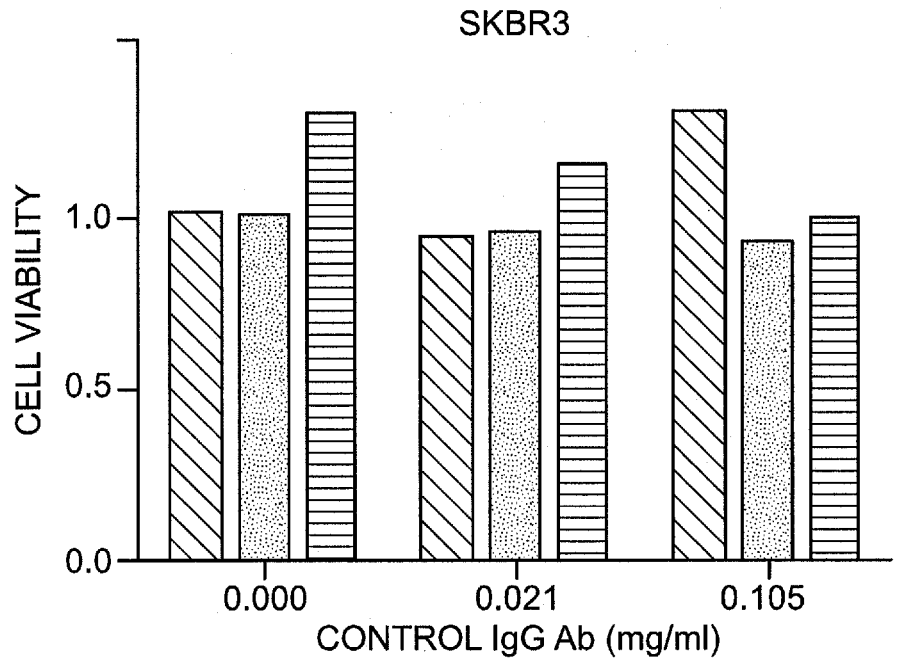
FIG. 1 shows cytotoxicity of trastuzumab and peripheral blood mononuclear cells on SKBR3 breast cancer cells. The SKBR3 tumor cells were sowed on a 35-mm dish in an amount of $1 \times 10^5$ cells, and trastuzumab and the peripheral blood mononuclear cells sampled from healthy individuals were added 24 hours later. Further, the number of viable tumor cells was determined 24 hours later. The mean and the standard deviation of triplicate assays are shown. Statistical analysis was carried out via two-way ANOVA. (A: group to which control antibody was administered; B: group to which trastuzumab was administered)

Hereafter, the present invention is described in detail.

The method of the present invention comprises:

step (a) of selectively reducing KLRG1-positive immunocytes in the peripheral blood of a living individual with epithelial cancer ex vivo, which is positive for a cancer-specific membrane antigen expressed in epithelial cancer cells and positive for a KLRG1 ligand; and step (b) of administering, to the living individual, a therapeutic agent for cancer comprising an antibody reacting with the cancer-specific membrane antigen expressed in epithelial cancer cells and having antibody-dependent cell cytotoxicity.

Step (a) and step (b) may be carried out in any order without particular limitation. Preferably, step (b) is carried out during or after step (a).

The term "selectively reducing KLRG1-positive immunocytes" used herein refers a state in which adsorption of the KLRG1-positive immunocytes (B) is higher than that of the KLRG1-negative immunocytes (A). A correlation of B>A is sufficient, that of B/A>2 is preferable, that of B/A>3 is more preferable, and that of B/A>4 is most preferable.

According to the method of the present invention, a therapeutic agent for cancer is preferably administered during or after step (a) of selectively reducing KLRG1-positive immunocytes from the peripheral blood of the living individual by extracorporeal circulation using the cell adsorbers having higher affinity for KLRG1-positive immunocytes than for KLRG1-negative immunocytes. The term "after step (a)" refers to a period of time during which the effects of step (a) are sustained, starting from immediately after the implementation of step (a). The term "during step (a)" refers to a period of time from the initiation to the completion of step (a). When step (a) is repeated a plurality of times as a set of treatments, the term "during step (a)" refers to a continuous period of time from the first treatment to the last treatment of step (a). When step (a) is a course of treatment in which extracorporeal circulation is performed once a week over a period of 3 months, and is carried out once or twice, for example, the term "during step (a)" refers to one or two courses of such treatment.

When administration of a therapeutic agent for cancer and selective reduction of KLRG1-positive immunocytes is independently carried out a plurality of times as a set of treatments, it is preferable that all the procedures for administration of therapeutic agents for cancer be carried out between the first and the last implementations of step (a) or after the last implementation.

The term "living individual" used herein extensively refers to living biological bodies. Examples include humans and animals other than humans, with humans being preferable. Specific examples include epithelial cancer patients.

In the present invention, examples of epithelial cancers include breast cancer, gastric cancer, ovarian cancer, lung cancer, esophageal cancer, colon cancer, duodenal cancer, pancreatic cancer, head and neck cancer, gallbladder cancer, biliary tract cancer, and salivary gland cancer, with breast cancer and gastric cancer being preferable.

Examples of the cancer-specific membrane antigen expressed in epithelial cancer cells include HER2, the carcinoembryonic antigen (CEA), mucin 1 (MUC-1), the epithelial cell adhesion molecule (EpCAM), the epidermal growth factor receptor (EGFR), the cancer antigen 125 (CA125), and tumor-associated glycoprotein-72 (TAG72), with HER2 and CEA being preferable.

Antibodies reacting with a cancer-specific membrane antigen expressed in epithelial cancer cells are not particularly limited, provided that such antibodies react with the aforementioned cancer-specific membrane antigens. Preferable examples include the anti-HER2 antibody and the anti-CEA antibody. A preferable example of the anti-HER2 antibody is trastuzumab.

In the present invention, KLRG1-positive immunocytes are selectively reduced from the peripheral blood of a living individual. Types of KLRG1-positive immunocytes are not particularly limited. Examples include KLRG1-positive NK cells and KLRG1-positive T cells, with KLRG1-positive NK cells being preferable.

Examples of KLRG1 ligands include those selected from the group consisting of E-cadherin, N-cadherin, and R-cadherin.

According to the present invention, preferably, the peripheral blood of a living individual is subjected to extracorporeal circulation, and the peripheral blood is brought into contact with a water-insoluble carrier on which a substance having affinity for KLRG1 has been immobilized to selectively reduce KLRG1-positive immunocytes in the peripheral blood of a living individual.

In the present invention, methods for selectively reducing KLRG1-positive immunocytes in the peripheral blood of a living individual are not particularly limited. For example, an apparatus having an inlet and an outlet and having means for selectively reducing KLRG1-positive immunocytes from the peripheral blood may be used to allow the peripheral blood to flow through the inlet, and the peripheral blood from which the KLRG1-positive immunocytes have been selectively reduced and which is discharged through the outlet is recovered. Thus, the KLRG1-positive immunocytes can be selectively reduced from the blood. The peripheral blood from which the KLRG1-positive immunocytes have been selectively reduced and which is discharged through the outlet may be returned into the body to selectively reduce the KLRG1-positive immunocytes in the peripheral blood of a living individual.

An example of a means for selectively reducing KLRG1-positive immunocytes that can be used in the present invention is a water-insoluble carrier on which a substance having affinity for KLRG1 is immobilized. Examples of substances having affinity for KLRG1 that can be used include an antibody reacting with KLRG1 or a fragment thereof and KLRG1 ligands, such as E-cadherin, N-cadherin, R-cadherin, or a fragment of any thereof. A variety of water-insoluble carriers can be used without particular limitation. Examples thereof include a porous body, a flat membrane, a nonwoven fabric, a woven fabric, and particles (e.g., magnetic particles), with magnetic particles or nonwoven fabric being preferable. When a water-insoluble carrier is a nonwoven fabric, a monofilament or multifilament may be used, and a porous or atypical filament may be used.

When a water-insoluble carrier is in a particulate form, spherical forms, polygonally spherical forms, or any other forms can be useful. A smooth or irregular surface may be used, provided that such surface is capable of selectively reducing KLRG1-positive immunocytes. The particle diameter is preferably between 50 μm and 10 mm. A particle diameter of less than 50 μm is not preferable since prevention of particle discharge is likely to become difficult. A particle diameter of more than 10 mm is not preferable since the size of a surface area is likely to be insufficient. The particle diameter is preferably 80 μm to less than 8 mm, and most preferably 100 μm to less than 6 mm.

A variety of materials can be used for the water-insoluble carrier of the present invention without particular limitation, provided that such materials are less likely to damage blood cells. Examples include an organic polymer, an inorganic polymer, and a metal. An organic polymer is particularly preferable since it is excellent in processability, such as cutting. Examples of organic polymeric materials include: naturally-occurring polymers, such as cellulosic materials, such as cellulose, cellulose monoacetate, cellulose diacetate, or cellulose triacetate, and/or derivatives thereof; polyesters, such as polyethylene terephthalate and polybutylene terephthalate; polyolefins, such as polyethylene and polypropylene; and polymeric materials, such as polyvinylidene fluoride, polyamide, polyimide, polyurethane, polysulfone, and polyacrylonitrile. Also, materials having surfaces that have been modified with hydrophilic polymeric materials via coating, radiation grafting, or other means for the purpose of imparting hydrophilic properties to such materials can be useful.

In the present invention, for example, a column having a blood inlet and a blood outlet may be used to allow the peripheral blood to flow through the blood inlet into an apparatus equipped with a water-insoluble carrier on which a substance having affinity for KLRG1 has been immobilized. Thus, KLRG1-positive immunocytes can be selectively reduced from the peripheral blood. The adsorption column may be connected to the extracorporeal circulation system used for blood purification therapy or other techniques to implement the present invention.

The treatment of the present invention involving extracorporeal circulation as described above can be generally carried out by circulating the blood at a flow rate of 30 ml/minute for 30 minutes to 90 hours per instance of treatment, although it varies depending on, for example, the target and the disease conditions of the target. The flow rate and duration can be adequately determined in accordance with, for example, the quantity or adsorption properties of the carrier to be used. Also, the treatment of the present invention via extracorporeal circulation as described above may be carried out before or during the administration of an antibody reacting with a cancer-specific membrane antigen. When extracorporeal circulation is carried out to selectively reduce KLRG1-positive immunocytes before antibody administration, an antibody is administered after the extracorporeal circulation treatment while the effects of extracorporeal circulation treatment are sustained. The term "during the administration of an antibody" refers to the period of time from the initiation of antibody administration to the completion thereof. When antibody administration is carried out a plurality of times as a set of treatments, the term refers to the continuous period of time from the first to the last antibody administration. When a course of treatment that involves performance of antibody administration once in two or three weeks is carried out over the period of 3 months and such course of treatment is carried out once or twice, for example, the term "during the administration of an antibody" refers to one or two courses of such treatment.

According to the present invention, the blood is subjected to contact processing by the batch method, and the pooled blood can be administered intravenously. This treatment can be implemented substantially in accordance with treatment involving extracorporeal circulation. The amount of the sampled blood and the amount of the treated blood to be administered are each approximately 150 to 450 ml per day, in general.

When treating the blood, an anticoagulant can be added to the blood for blood anticoagulation purposes. Any anticoagulant can be used without particular limitation, provided that such compound has anticoagulation activity. Preferable examples thereof include heparin, low-molecular-weight heparin, nafamostat mesilate, gabexate mesilate, Argatroban, and sodium citrate, with heparin or nafamostat mesilate being more preferable.

According to the present invention, further, an extracorporeal circulation system comprising: (1) a blood sampling means; (2) a blood circulating means; (3) an apparatus having a blood inlet and a blood outlet and having a means for selectively reducing KLRG1-positive immunocytes from the blood; and (4) a retransfusion means may be used to selectively reduce KLRG1-positive immunocytes in the peripheral blood of a living individual.

The blood sampling means is a part of an apparatus used for extracting blood. Examples thereof include a spike needle, a reservoir syringe, a blood collection needle, and a catheter. The retransfusion means is a part of an apparatus used for retransfusing blood. Examples include those used for the blood sampling means. The blood circulating means is, for example, a conduit pipe in which blood flows. The conduit pipe may be in any shape, provided that it is hollow. Any material can be used for a conduit pipe, provided that such material would not adversely affect the blood to a significant extent. Examples of such materials include polyvinyl chloride, polyethylene, and polypropylene.

As the "the cell adsorber having higher affinity for KLRG1-positive immunocytes than for KLRG1-negative immunocytes" used in the present invention, an apparatus comprising a means for selectively reducing KLRG1-positive immunocytes, such as a water-insoluble carrier on which a substance having affinity for KLRG1 has been immobilized as described above, can be used. The "cell adsorber having higher affinity for KLRG1-positive immunocytes than for KLRG1-negative immunocytes" of the present invention can be used for selectively reducing KLRG1-positive immunocytes in the peripheral blood by subjecting the peripheral blood to extracorporeal circulation before or during the administration of a therapeutic agent for cancer comprising an antibody having antibody-dependent cell cytotoxicity against the cancer-specific membrane antigen expressed in epithelial cancer cells to a living individual having epithelial cancer, which is positive for the cancer-specific membrane antigen and positive for the KLRG1 ligand.

The present invention is described in greater detail with reference to the following examples, although the present invention is not limited thereto.

EXAMPLES

Example 1

(A) Method (1) Cell Line

HER2-positive human breast cancer cell lines (SKBR3 and HCC1569) were purchased from ATCC. SKBR3 was confirmed to be pan-cadherin-negative and E- and N-cadherin-negative. In contrast, HCC1569 was confirmed to be pan-cadherin-positive and E- and N-cadherin-positive. SKBR3 was cultured in DMEM (Dulbecco's modified Eagle's medium) (Sigma Aldrich, Mo., U.S.A.) with the addition of fetal bovine serum (FBS, Invitrogen Corporation, U.S.A.), penicillin, and streptomycin. HCC1569 was cultured in RPMI-1640 medium (Sigma Aldrich, Mo., U.S.A.) with the addition of fetal porcine serum, penicillin, and streptomycin.

(2) siRNA

As CDH1 and CDH2 siRNA, Silencer Select Pre-designed siRNA (Ambion Inc., U.S.A.) was purchased and used. Silencer Select Negative control#1 siRNA (Ambion) was used as a control. The final concentration of siRNA was set at 5 nM. Synthetic siRNA was introduced into a cell using DamaFECT Transfection Reagents 2 (Darmacon Inc., U.S.A.).

The breast cancer cells (HCC1569) were sowed in a 6-well plate at $5\times10^5$ cells/well and cultured in an incubator at 37° C. in the presence of 5% $CO_2$ overnight. Regarding the molecules to be subjected to single-knockdown, 2 µl of 2 µM siRNA was added to 198 µl of OPTI-MEM (Invitrogen Inc., U.S.A.), 2 µl of another 2 µM siRNA was added to 4 µl of a reagent and 196 µl of OPTI-MEM, the resultants were mixed with each other, and the resulting mixture was incubated at room temperature for 20 minutes to form a complex. Regarding the molecules to be subjected to double-knockdown, 2 µl of another 2 µM siRNA was added to 196 µl of OPTI-MEM, 2 µl of another 2 µM siRNA was added to 8 µl of a reagent and 192 µl of OPTI-MEM, and the resulting mixtures were treated in the same manner as with the case of the molecules to be subjected to single-knockdown. The culture solution in the 6-well plate used for culture on the previous day was suctioned, and 1,600 µl of OPTI-MEM was added. Thereafter, the complex was added to the wells in amounts of 200 µl each and cultured in an incubator at 37° C. in the presence of 5% $CO_2$. mRNA was extracted from cells 48 hours later, and the effects of RNAi were analyzed via quantitative real-time RT-PCR.

RNA was extracted with the use of Trizol Reagent (Invitrogen). The 6-well plate was washed with PBS, 1 ml of Trizol was added thereto, and cells were scraped from the plate with the use of a cell scraper and transferred to a 1.5-ml tube. Subsequently, 0.2 ml of chloroform was added to 1 ml of Trizol, and the resultant was centrifuged at 15,000 rpm for 5 minutes. The uppermost layer of the three resulting separate layers was transferred to another tube, isopropanol was added thereto in an amount of 0.5 ml/ml, and the resultant was centrifuged at 15,000 rpm for 5 minutes. The supernatant was removed, and the pellet was washed with 75% ethanol and dried at room temperature. Rnase-free water (10 µl) was added, and the resultant was allowed to stand at room temperature for 30 minutes for pellet dissolution. Thereafter, RNA expression was assayed via quantitative real-time RT-PCR.

Reverse transcription was carried out using the PrimeScript RT reagent Kit (TaKaRa). PrimeScript Buffer (2 µl, for real-time), 0.5 µl of PrimeScript RT Enzyme MixI, 0.5 µl of Random 6 mers, and 6 µA of Rnase Free dH20 were added to 1 µg of total RNA, and reverse transcription was carried out at 37° C. for 15 minutes to obtain cDNA.

In order to prepare samples of known concentrations and copy numbers used for the preparation of a calibration curve, CDH1, CDH2, and GAPDH primers were used, the HCC1569 cells cultured in a static state were used as a template, and a PCR product was obtained. In order to prepare a calibration curve, standard samples of five different dilution ratios were prepared. GAPDH was designated as the endogenous reference gene.

Quantitative real-time RT-PCR was carried out with the use of the Smart Cycler II System (TaKaRa, Japan). A mixture of 12.5 µl of SYBR Green I, 1 µl each of 10 µM primers (forward and reverse primers), 2 µl each of cDNAs obtained via reverse transcription, and 8.5 µl of distilled water was added to a reaction tube.

The PCR product is quantified based on the fluorescence level of a fluorescent dye, SYBR Green. The amplification curve of the PCR product is drawn based on the fluorescence level of the SYBR Green, and a calibration curve is prepared by designating the cycle number at which the amplification curve crosses a threshold value as the threshold cycle ($C_\gamma$). The amount of target RNA can be deduced based on the resulting calibration curve. The $C_\gamma$ value of the target gene was standardized in comparison with the endogenous reference gene (GAPDH).

(3) Trastuzumab and Antibody

Trastuzumab was purchased from Chugai Pharmaceutical Co., Ltd. Mouse IgGκ isotype (BioLegend, U.S.A.) was purchased and used as a control antibody. A rabbit anti-human KLRG1 antibody (Santa Cruz Biotechnology, U.S.A.) was used for recognition of the KLRG1 receptor on the NK cells.

(4) Treatment of Peripheral Blood Mononuclear Cells

The peripheral blood was sampled from healthy individuals, and the mononuclear cell layer was recovered via Ficoll-Hypaque gradient centrifugation at 3,300 rpm for 30 minutes with the use of the Vacutainer blood collection tube (BD, U.S.A.). The recovered peripheral blood mononuclear cells were labeled with the rabbit anti-human KLRG1 antibody and with goat anti-rabbit IgG MicroBeads (MiltenyiBiotec GmbH, Gladbach, Germany), and the KLRG1-expressing cells were removed with the use of the MACS MS column.

(5) Examination of Cytotoxicity with the Use of Peripheral Blood Mononuclear Cells The two types HER2-positive breast cancer cell lines, the SKBR3 cells (pan-cadherin negative) and the HCC1569 cells (pan-cadherin positive: E-cadherin positive, N-cadherin positive), were subjected to the following examination.

(5-1) Tumor cells (T) were sowed on a 35-mm dish in amounts of $1\times10^5$ cells, trastuzumab and the peripheral blood mononuclear cells (E) sampled from healthy individuals were added 24 hours later, and the number of viable tumor cells was determined 24 hours thereafter. Trastuzumab was added at different concentrations of 0, 0.021, and 0.105 mg/ml. The ratios of the tumor cells to the peripheral blood mononuclear cells (T:E) were set at 1:0, 1:1, and 1:20.

(5-2) The HER2-positive breast cancer cell line, HCC1569 (pan-cadherin positive, E-cadherin positive, and N-cadherin positive), was subjected to E-cadherin (CDH1) and/or N-cadherin (CDH2) knockdown, and the cell line was examined in the same manner as in (5-1).

(5-3) The peripheral blood mononuclear cells were sorted in accordance with the occurrence of KLRG1 expression, and the cells were examined in the same manner as in (5-1) with the use of the peripheral blood mononuclear cells from which the KLRG1-positive cells had been removed.

(6) ADCC Assay

ADCC assay with the use of the peripheral blood mononuclear cells was carried out via the $^{51}$Cr release test. The peripheral blood mononuclear cells sampled from healthy individuals were used as effector cells (E), and the HCC1569 cells in which E-cadherin or N-cadherin had been knocked down via introduction of SKBR3, HCC1569, siRNA CDH1, or siRNA CDH2 were used as the target cells (T). The target cells ($1\times10^6$ cells) were cultured in the presence of 50 μl of $Na_2^{51}CrO_4$ (Perkin Elmer, Japan) in an incubator at 37° C. in the presence of 5% $CO_2$ for 1.5 hours, and the target cells were labeled with $^{51}$Cr chromic acid. The labeled target cells ($5\times10^3$ cells) were suspended in 50 μl of a culture solution, the suspension was sowed on a 96-well U-bottom plate, and mononuclear cells were added to the wells at a T:E ratio of 1:0, 1:1, 1:20, or 1:50. Further, trastuzumab (21 μg/ml) or a control (the mouse IgG1 antibody (21 μg/ml) or a culture solution alone) was added in an amount of 100 μl to each of the wells, and coculture was carried out in an incubator at 37° C. in the presence of 5% $CO_2$ for 4 hours. Thereafter, the culture product was centrifuged at 1,500 rpm for 5 minutes, 50 μl of the supernatant was sampled, and the radioactivity was assayed with the use of a γ counter. The percent-specific $^{51}$Cr release value was determined by the following equation and the resulting value was designated as representing ADCC activity.

ADCC activity=100×($^{51}$Cr release when effector cells were added−spontaneous $^{51}$Cr release when effector cells were not added)/(maximal $^{51}$Cr release upon addition of Triton X without addition of effector cells−spontaneous $^{51}$Cr release when effector cells were not added)

Figure 1B:
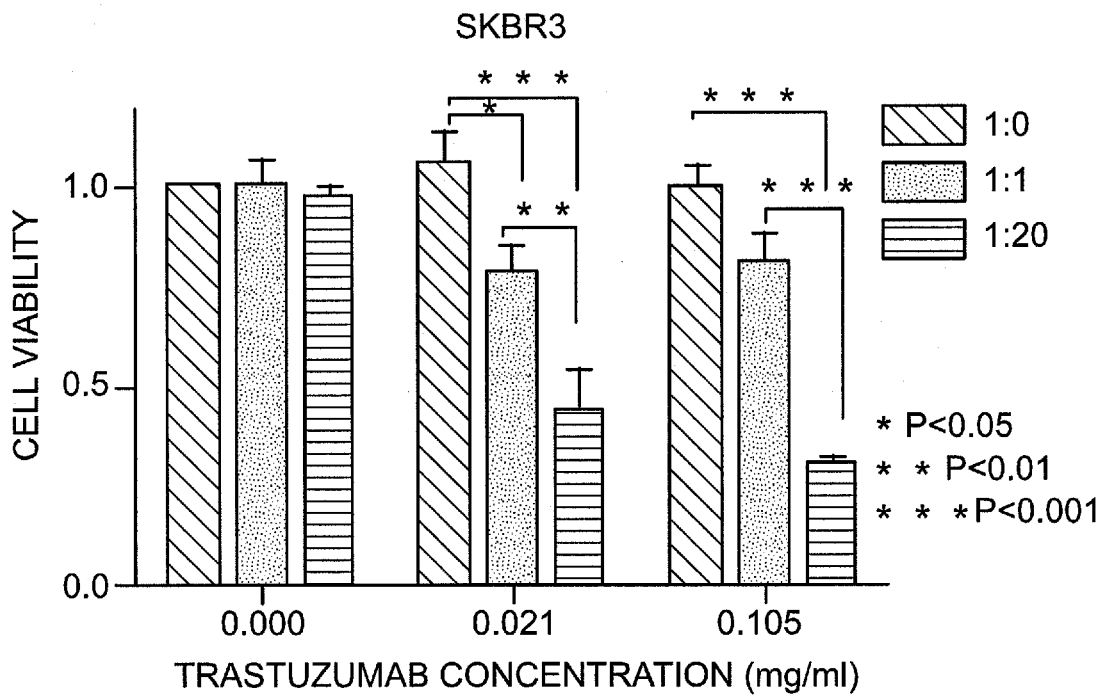

(B) Results (1) Cytotoxicity of Trastuzumab and Peripheral Blood Mononuclear Cells on SKBR3 Breast Cancer Cell (FIG. 1)

In order to convert trastuzumab-resistance cases into trastuzumab-effective cases, methods for confirmation and derepression of ADCC activity with the use of NK cells were examined. As a result, no change was observed in SKBR3 (pan-cadherin negative) in terms of tumor cell viability at a trastuzumab concentration of 0, 0.021 mg/ml, or 0.105 mg/ml when the peripheral blood mononuclear cells were not cultured together. When the trastuzumab concentration was set at 0, no change was observed in tumor cell viability even when the tumor cells were cultured with the same or 20 times greater the amount of the peripheral blood mononuclear cells. When the trastuzumab concentration was set at 0.021 mg/ml and the tumor cells were cultured with the same amount of the peripheral blood mononuclear cells, tumor cell viability was significantly lowered, compared with a case in which the peripheral blood mononuclear cells were not cultured together. When the tumor cells were cultured with 20 times greater the amount of the peripheral blood mononuclear cells, tumor cell viability was further lowered, and tumor cell viability was significantly lowered, compared with a case in which the peripheral blood mononuclear cells were not cultured together and in which the tumor cells were cultured with the same amount of the peripheral blood mononuclear cells. When the trastuzumab concentration was set at 0.105 mg/ml, tumor cell viability was lowered when the tumor cells were cultured with 20 times greater the amount of the peripheral blood mononuclear cells. That is, tumor cell viability was significantly lowered, compared with a case in which the peripheral blood mononuclear cells were not cultured together and in which the tumor cells were cultured with the same amount of the peripheral blood mononuclear cells. When the tumor cells were cultured with the same amount of the peripheral blood mononuclear cells, tumor cell viability was likely to be lowered, compared with a case in which the peripheral blood mononuclear cells were not cultured together, although no statistically significant difference was observed. The results demonstrate that tumor cell viability of SKBR3, which would not involve cadherin expression, would be lowered depending on the number of peripheral blood mononuclear cells, regardless of the trastuzumab concentration (FIG. 1).

Figure 2A:
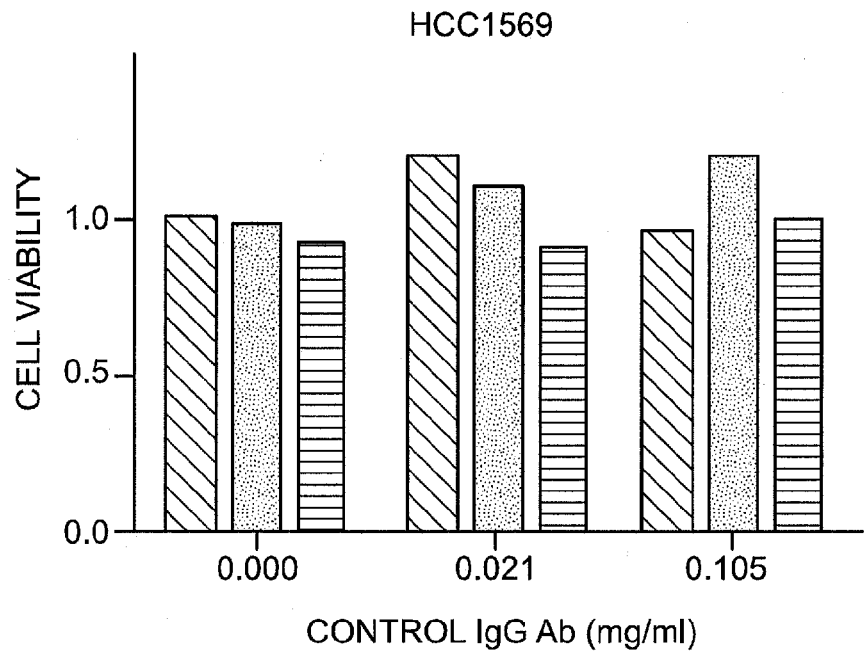
FIG. 2 shows cytotoxicity of trastuzumab and peripheral blood mononuclear cells on HCC1569 breast cancer cells. The HCC1569 tumor cells were sowed on a 35-mm dish in an amount of $1 \times 10^5$ cells, and trastuzumab and the peripheral blood mononuclear cells sampled from healthy individuals were added 24 hours later. Further, the number of viable tumor cells was determined 24 hours later. The mean and the standard deviation of triplicate assays are shown. Statistical analysis was carried out via two-way ANOVA. (A: the control group; B: group to which trastuzumab was administered)
Figure 2B:
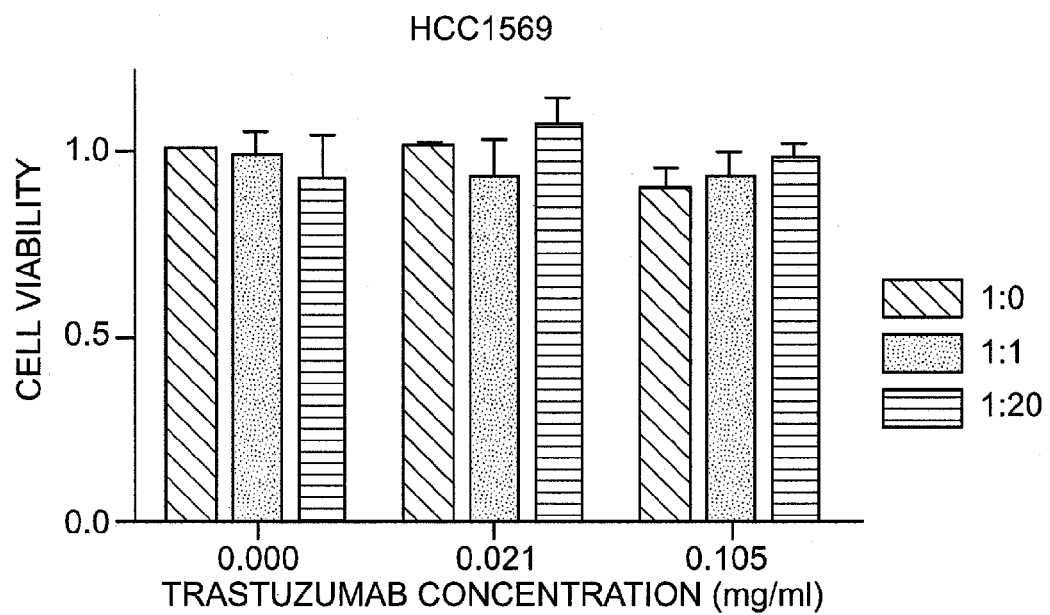

(2) Cytotoxicity of Trastuzumab and Peripheral Blood Mononuclear Cells on HCC1569 Breast Cancer Cells (FIG. 2)

No change was observed in the HCC1569 cells (pan-cadherin positive, E-cadherin positive, and N-cadherin positive) in terms of tumor cell viability at a trastuzumab concentration of 0, 0.021 mg/ml, or 0.105 mg/ml, when the peripheral blood mononuclear cells were not cultured together. When the trastuzumab concentration was set at 0, also, no change was observed in tumor cell viability even when the tumor cells were cultured with the same or 20 times greater the amount of the peripheral blood mononuclear cells. When the trastuzumab concentration was set at 0.021 mg/ml and the tumor cells were cultured with the same amount of the peripheral blood mononuclear cells, further, no change was observed in tumor cell viability, as with the case in which the peripheral blood mononuclear cells were not cultured together. No change was observed in tumor cell viability when the tumor cells were cultured with 20 times greater the amount of the peripheral blood mononuclear cells. Such tendency was also observed when the trastuzumab concentration was set at 0.105 mg/ml, and no change was observed in tumor cell viability even when the tumor cells were cultured with the same or 20 times greater the amount of the peripheral blood mononuclear cells. The results demonstrate that tumor cell viability of HCC1569 involving cadherin expression would not be changed regardless of the trastuzumab concentration and the peripheral blood mononuclear cell count (FIG. 2).

Figure 3A:
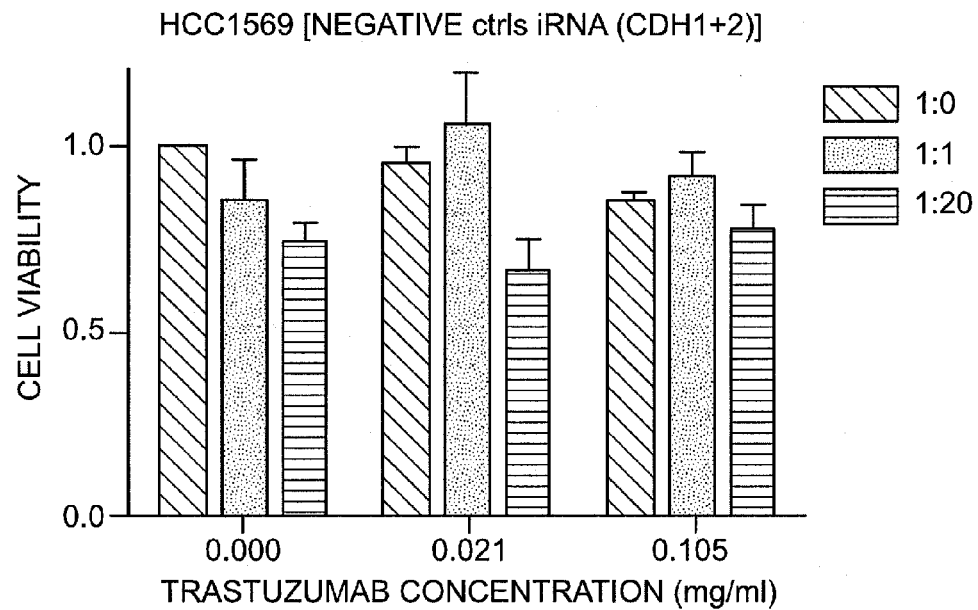
FIG. 3 shows the effects of E-cadherin and N-cadherin suppression on cytotoxicity of trastuzumab and peripheral blood mononuclear cells on HCC1569 breast cancer cells. The HCC1569 cells in which cadherin had been knocked down by siRNA were sowed on a 35-mm dish in an amount of $1 \times 10^5$ cells, and trastuzumab and the peripheral blood mononuclear cells sampled from healthy individuals were added 24 hours later. Further, the number of viable tumor cells was determined 24 hours later. The mean and the standard deviation of triplicate assays are shown. Statistical analysis was carried out via two-way ANOVA. (A: control; B: E-cadherin and N-cadherin knocked down HCC1569)
Figure 3B:
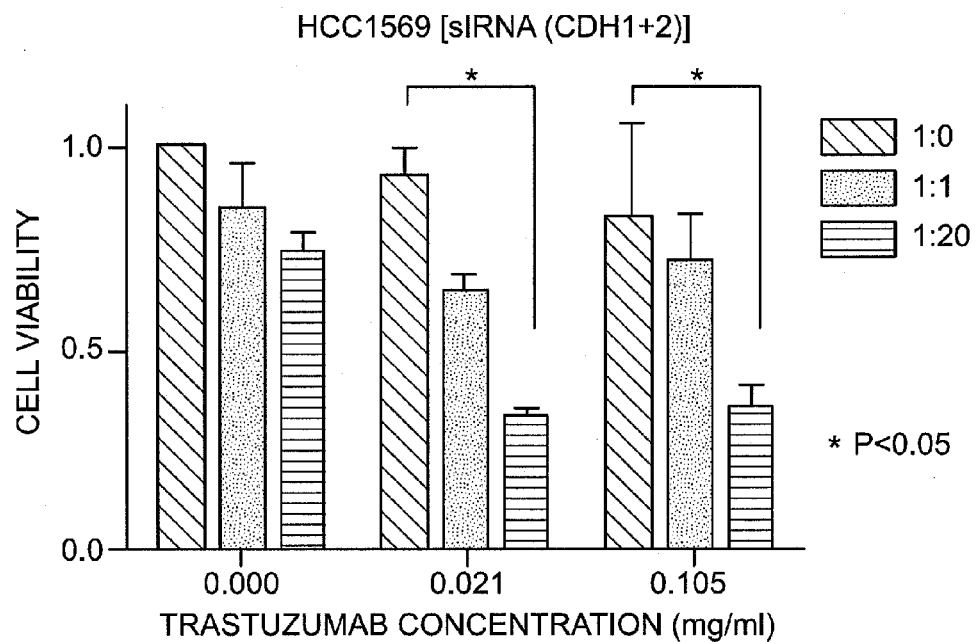

(3) Effects of E-Cadherin and N-Cadherin Suppression on Cytotoxicity of Trastuzumab and Peripheral Blood Mononuclear Cells on HCC1569 Breast Cancer Cells (FIG. 3)

In the HCC1569 cells subjected to double-knockdown of E-cadherin (CDH1) and N-cadherin (CDH2), no change was observed in tumor cell viability at a trastuzumab concentration of 0, 0.021 mg/ml, or 0.105 mg/ml, when the peripheral blood mononuclear cells were not cultured together. When the trastuzumab concentration was set at 0, also, no statistically significant difference was observed in tumor cell viability even when the tumor cells were cultured with the same or 20 times greater the amount of the peripheral blood mononuclear cells. When the trastuzumab concentration was set at 0.021 mg/ml and 0.105 mg/ml and the tumor cells were cultured with 20 times greater the amount of the peripheral blood mononuclear cells, however, tumor cell viability was significantly lowered, compared with a case in which the peripheral blood mononuclear cells were not cultured together. When the tumor cells were cultured with the same amount of the peripheral blood mononuclear cells, tumor cell viability was likely to be lowered, although no statistically significant difference was observed (FIG. 3).

The test on the tumor cells demonstrates that tumor cell viability of the pan-cadherin negative tumor cells would be lowered depending on the number of peripheral blood mononuclear cells, regardless of the trastuzumab concentration. In pan-cadherin positive tumor cells, also, the number of viable tumor cells was not likely to decrease depending on the number of peripheral blood mononuclear cells, regardless of the trastuzumab concentration.

Figure 4A:
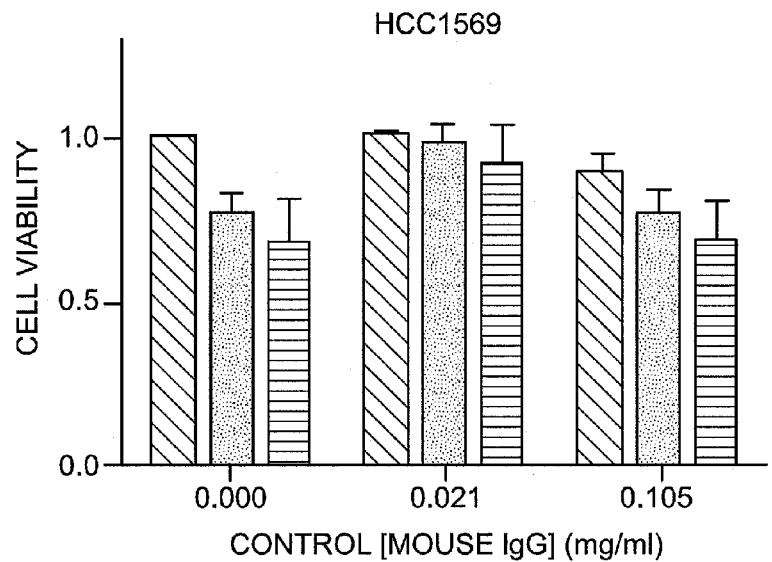
FIG. 4 shows cytotoxicity of trastuzumab and peripheral blood mononuclear cells from which KLRG1-expressing cells had been removed on the HCC1569 breast cancer cells. The HCC1569 (T) tumor cells were sowed on a 35-mm dish in an amount of $1 \times 10^5$ cells, trastuzumab and peripheral blood mononuclear cells sampled from healthy individuals were subjected to sorting, peripheral blood mononuclear cells (E) from which KLRG1-expressing cells had been removed were added 24 hours later, and the number of viable tumor cells was determined 24 hours later. The mean and the standard deviation of triplicate assays are shown. Statistical analysis was carried out via two-way ANOVA. (A: control; B: HCC1569)
Figure 4B:
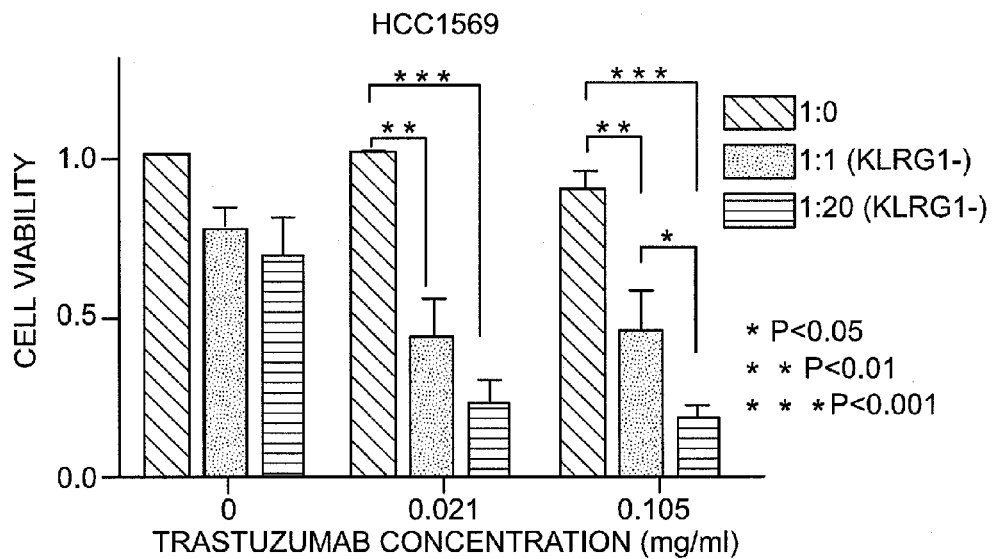

(4) Cytotoxicity of Trastuzumab and Peripheral Blood Mononuclear Cells from which KLRG1-Expressing Cells Had been Removed on HCC1569 Breast Cancer Cells (FIG. 4)

A similar experiment was carried out using the peripheral blood mononuclear cells from which the KLRG1-expressing cells had been removed.

In the untreated HCC1569 cells in which cadherin is expressed, no change was observed in tumor cell viability at a trastuzumab concentration of 0, 0.021 mg/ml, or 0.105 mg/ml, when the peripheral blood mononuclear cells were not cultured together. When the trastuzumab concentration was set at 0, no change was observed in tumor cell viability even when the tumor cells were cultured with the same or 20 times greater the amount of the peripheral blood mononuclear cells. When the trastuzumab concentration was set at 0.021 mg/ml and the tumor cells were cultured with the same amount of the peripheral blood mononuclear cells, however, tumor cell viability was significantly lowered, compared with a case in which the peripheral blood mononuclear cells were not cultured together. When the tumor cells were cultured with 20 times greater the amount of the peripheral blood mononuclear cells, tumor cell viability was further lowered, and tumor cell viability was significantly lowered, compared with a case in which the peripheral blood mononuclear cells were not cultured together. When the trastuzumab concentration was set at 0.105 mg/ml and the tumor cells were cultured with the same amount of the peripheral blood mononuclear cells, tumor cell viability was significantly lowered, compared with a case in which the peripheral blood mononuclear cells were not cultured together. When the tumor cells were cultured with 20 times greater the amount of the peripheral blood mononuclear cells, tumor cell viability was further lowered, and tumor cell viability was significantly lowered, compared with the cases in which the peripheral blood mononuclear cells were not cultured together and in which the tumor cells were cultured with the same amount of the peripheral blood mononuclear cells (FIG. 4).

Figure 5A:
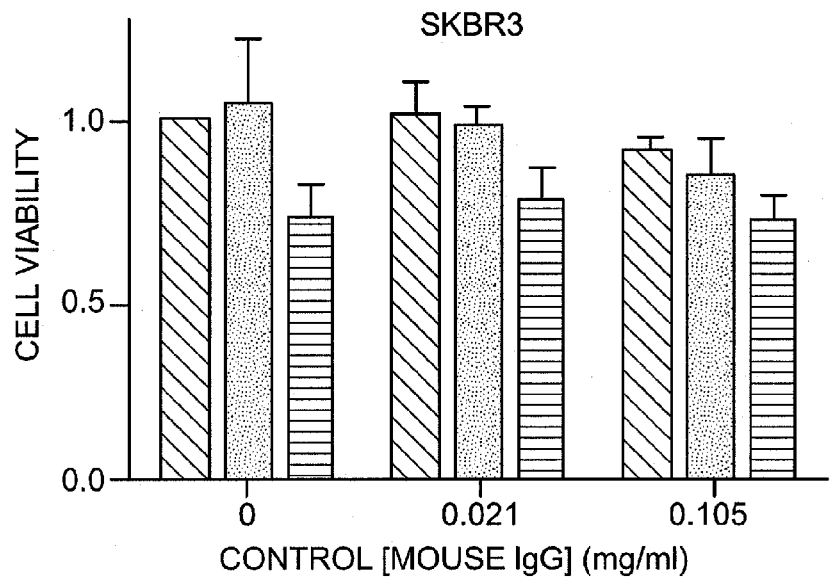
FIG. 5 shows cytotoxicity of trastuzumab and peripheral blood mononuclear cells from which KLRG1-expressing cells had been removed on the SKBR3 breast cancer cells. The SKBR3 (T) tumor cells were sowed on a 35-mm dish in an amount of $1\times10^5$ cells, and trastuzumab and peripheral blood mononuclear cells sampled from healthy individuals were subjected to sorting, with peripheral blood mononuclear cells (E) from which KLRG1-expressing cells had been removed being added 24 hours later. The number of viable tumor cells was determined 24 hours later. The mean and the standard deviation of triplicate assays are shown. Statistical analysis was carried out via two-way ANOVA. (A: control; B: SKBR3)
Figure 5B:
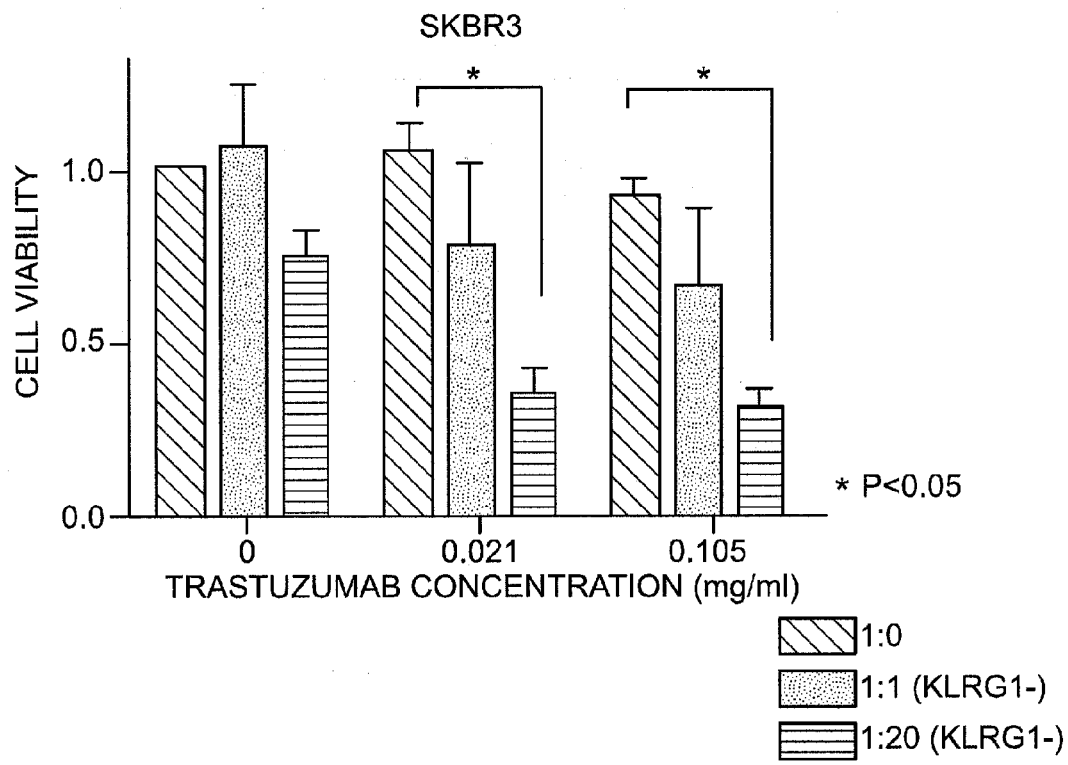

(5) Cytotoxicity of Trastuzumab and Peripheral Blood Mononuclear Cells from which KLRG1-Expressing Cells Had been Removed on SKBR3 Breast Cancer Cells (FIG. 5)

In the case of SKBR3 that would not involve cadherin expression, no change was observed in tumor cell viability at a trastuzumab concentration of 0, 0.021 mg/ml, or 0.105 mg/ml, when the peripheral blood mononuclear cells were not cultured together. When the trastuzumab concentration was set at 0, no change was observed in tumor cell viability even when the tumor cells were cultured with the same or 20 times greater the amount of the peripheral blood mononuclear cells. When the trastuzumab concentration was set at 0.021 mg/ml and the tumor cells were cultured with 20 times greater the amount of the peripheral blood mononuclear cells, however, the number of viable tumor cells decreased, and tumor cell viability was significantly lowered, compared with a case in which the peripheral blood mononuclear cells were not cultured together. When the tumor cells were cultured with the same amount of the peripheral blood mononuclear cells, tumor cell viability was likely to be lowered, compared with a case in which the peripheral blood mononuclear cells were not cultured together, although no statistically significant difference was observed. When the trastuzumab concentration was set at 0.105 mg/ml and the tumor cells were cultured with 20 times greater the amount of the peripheral blood mononuclear cells, tumor cell viability was significantly lowered, compared with a case in which the peripheral blood mononuclear cells were not cultured together. When the tumor cells were cultured with the same amount of the peripheral blood mononuclear cells, tumor cell viability was likely to be lowered, compared with a case in which the peripheral blood mononuclear cells were not cultured together, although no statistically significant difference was observed (FIG. 5).

Figure 6A:
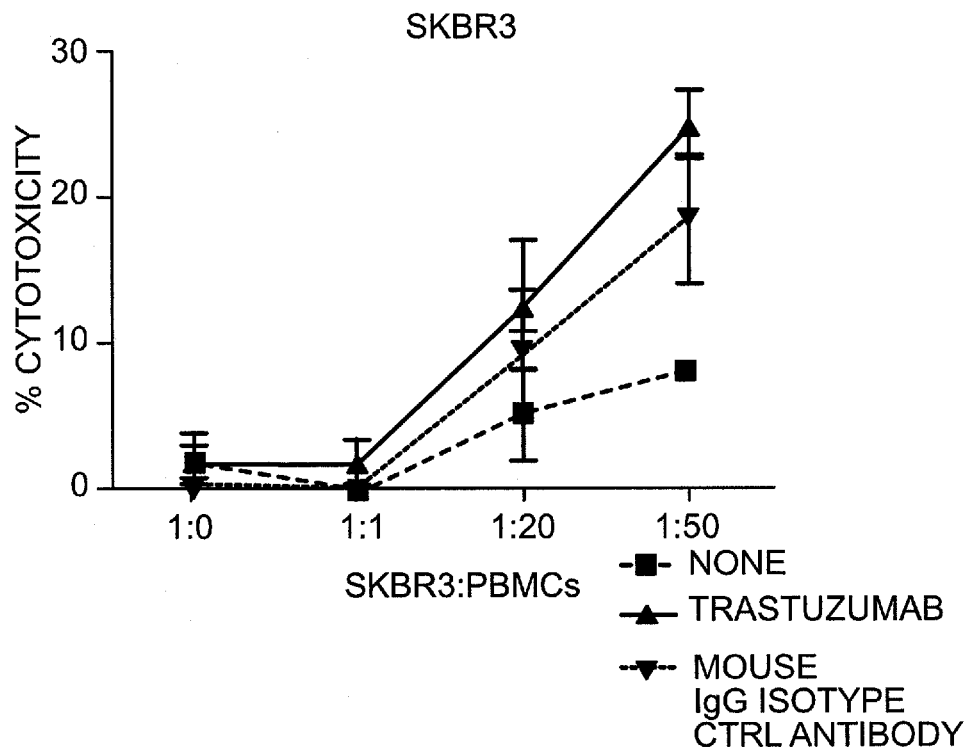
FIG. 6 shows the effects of KLRG1 expression in peripheral blood mononuclear cells on ADCC activity against SKBR3 breast cancer cells. The SKBR3 (T) tumor cells ($1\times10^6$ cells) were cultured in the presence of 50 μl of $Na_2{}^{51}CrO_4$ in an incubator at 37° C. in the presence of 5% $CO_2$ for 1.5 hours, the labeled $5\times10^3$ SKBR3 cells were sowed on a 96-well plate, mononuclear cells (E) were added to the wells at a T:E ratio of 1:0, 1:1, 1:20, or 1:50, coculture was carried out in an incubator at 37° C. in the presence of 5% $CO_2$ for 4 hours, and the radioactivity of $^{51}Cr$ released from the tumor cells was assayed. The mean and the standard deviation of triplicate assays are shown. (A: untreated peripheral blood mononuclear cells; B: peripheral blood mononuclear cells from which KLRG1-expressing cells were removed)
Figure 6B:
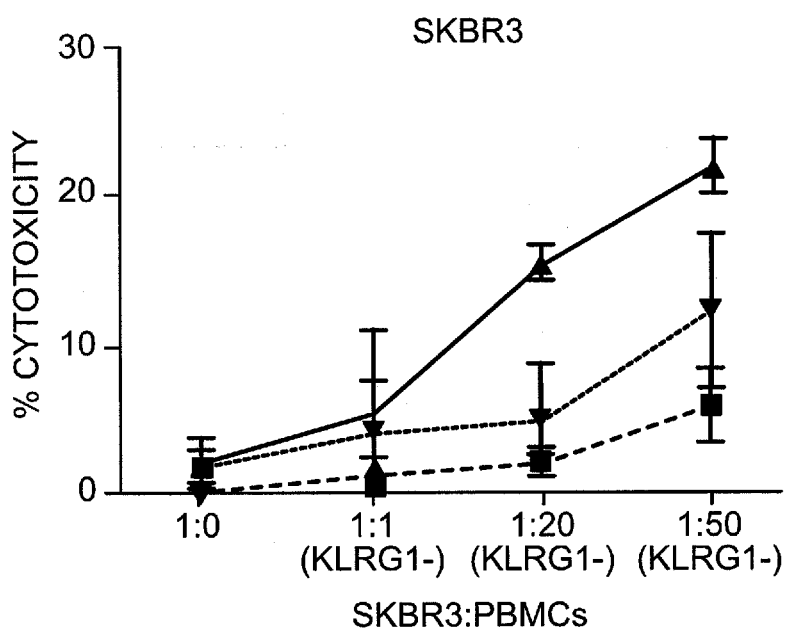
Figure 7A:
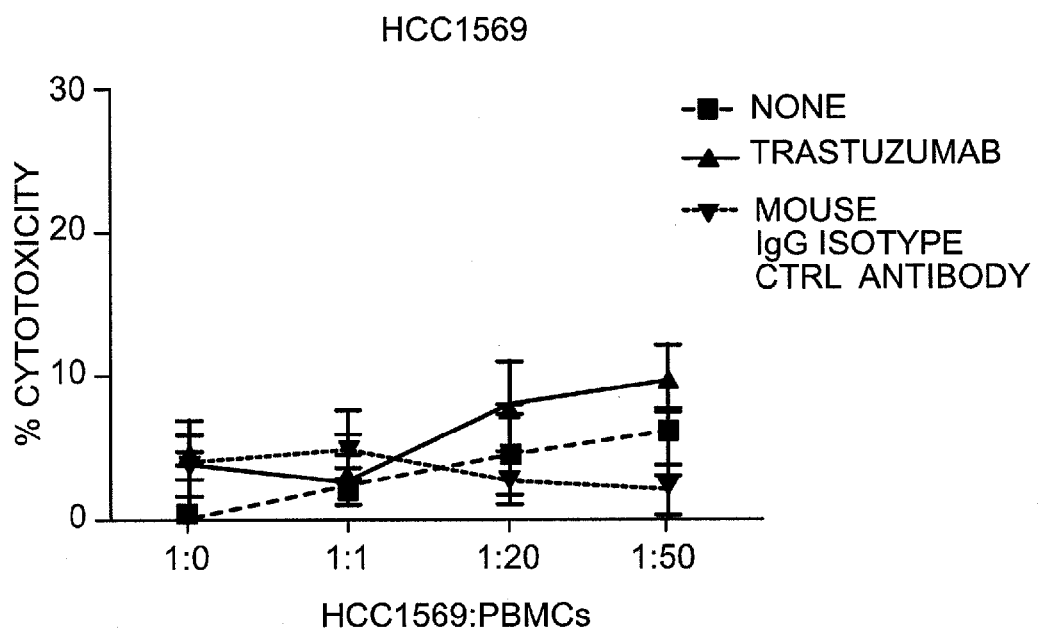
FIG. 7 shows the effects of KLRG1 expression in peripheral blood mononuclear cells on ADCC activity against HCC1569 breast cancer cells. The HCC1569 (T) tumor cells ($1\times10^6$ cells) were cultured in the presence of 50 μl of $Na_2{}^{51}CrO_4$ in an incubator at 37° C. in the presence of 5% $CO_2$ for 1.5 hours, the labeled $5\times10^3$ HCC1569 cells were sowed on a 96-well plate, mononuclear cells (E) were added to the wells at a T:E ratio of 1:0, 1:1, 1:20, or 1:50, coculture was carried out in an incubator at 37° C. in the presence of 5% $CO_2$ for 4 hours, and the radioactivity of $^{51}Cr$ released from the tumor cells was assayed. The mean and the standard deviation of triplicate assays are shown. (A: untreated peripheral blood mononuclear cells; B: peripheral blood mononuclear cells from which KLRG1-expressing cells were removed)
Figure 7B:
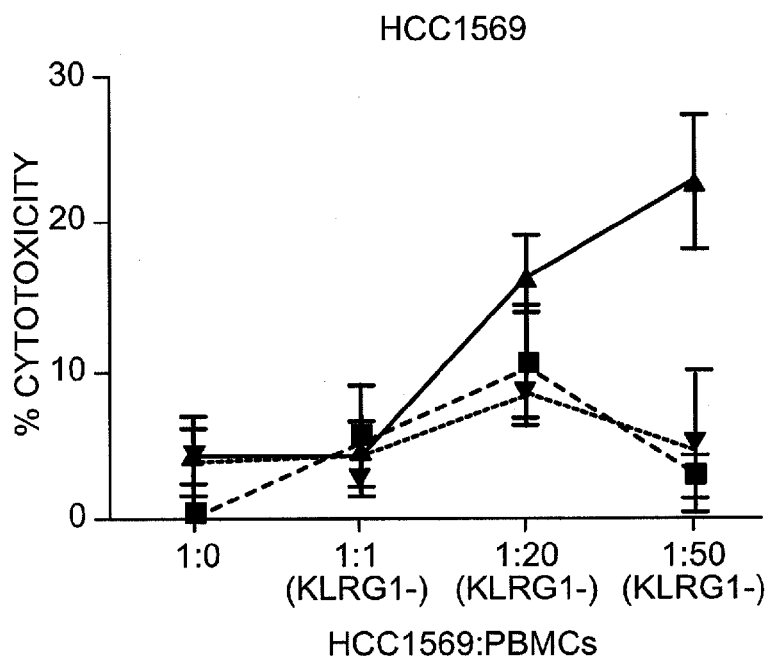

(6) Effects of KLRG1 Expression in Peripheral Blood Mononuclear Cells on ADCC Activity against SKBR3 Breast Cancer Cells (FIG. 6) and Effects of KLRG1 Expression in Peripheral Blood Mononuclear Cells on ADCC Activity Against HCC1569 Breast Cancer Cells (FIG. 7)

As a result of the 4 h-$^{51}$Cr release test, which was conducted for further confirmation, cytotoxicity on SKBR3 was observed depending on the number of peripheral blood mononuclear cells, regardless of KLRG1 expression (FIG. 6). When the untreated HCC1569 cells were examined with the use of the untreated peripheral blood mononuclear cells, ADCC activity was not observed regardless of the peripheral blood mononuclear cell count. In the untreated HCC1569 cells, however, trastuzumab-induced ADCC activity was observed as a result of an examination using peripheral blood mononuclear cells from which the KLRG1-expressing cells had been removed. This depends on the number of peripheral blood mononuclear cells (FIG. 7).

(C) Summary

Among the HER2-positive human breast cancer cell lines, the E-cadherin- or N-cadherin-positive cell lines are resistant to trastuzumab. By lowering the E- and N-cadherin expression levels, however, trastuzumab resistance of such cell lines was attenuated. As a result of examination of the mechanisms of trastuzumab with which cadherin is involved, cadherin was confirmed to be involved in ADCC activity, which is a main mechanism of trastuzumab. It was thus deduced that the immunological mechanism was strongly associated with trastuzumab resistance. By selectively reducing the NK cells that express KLRG1 (i.e., the inhibitory receptors that recognize E- and N-cadherins in the NK cells as ligands), trastuzumab resistance was quenched.

Example 2

Preparation of Activated Nonwoven Fabric

N-hydroxymethyl-2-iodoacetamide (0.6 g), 5.7 ml of concentrated sulfuric acid, and 7.2 ml of nitrobenzene were added to a glass flask, the flask was subjected to agitation at room temperature to dissolve the contents, and 0.036 g of paraformaldehyde was further added, followed by agitation. Nonwoven polypropylene fabric (0.3 g, average fiber diameter: 3.8 μm; fiber weight per unit area: 80 g/m$^2$; thickness: approximately 0.55 mm) was introduced thereinto and subjected to a reaction at room temperature for 24 hours under light-shielded conditions. Thereafter, the nonwoven fabric was removed, washed with ethanol and pure water, and dehydrated in vacuo to obtain activated nonwoven fabrics.

The activated nonwoven fabric was cut into 4 circular pieces each with a diameter of 0.68 cm, the four circular pieces were soaked in calcium- and magnesium-free phosphate buffer (hereafter abbreviated as "PBS(−)") comprising 0.4 ml of the rabbit anti-human KLRG1 polyclonal antibody purified with an affinity column (SANTA CRUZ BIOTECHNOLOGY, INC.; hereafter abbreviated as the "anti-KLRG1 antibody") (16 μg of anti-KLRG1 antibody per 0.4 ml) at room temperature for 1 hour, and the resultant was further soaked for approximately 24 hours in cold storage (2° C. to 8° C.) to immobilize the anti-KLRG1 antibody. The activated nonwoven fabric samples on which the anti-KLRG1 antibody had been immobilized were superposed in a container having an inlet and an outlet (volume: about 1 ml), and the nonwoven fabric samples were washed with 3 ml of PBS(−) from the inlet of the container. Subsequently, 0.4 ml of a 0.2% polyoxyethylene sorbitan monolaurate/PBS(−) solution (hereafter abbreviated as a "Tween20 solution") was added, the fabric samples were soaked therein at room temperature for 2.5 hours, and the resultant was washed with 3 ml of PBS(−) to obtain KLRG1-positive cell adsorbers.

The four above KLRG1-positive cell adsorbers (average fiber diameter: 3.8 μm; fiber weight per unit area: 80 g/m$^2$; thickness: approximately 0.5 mm) and a 10 mM ascorbic acid solution in PBS(−) (a filling fluid, molecular weight of ascorbic acid: 176) were used to fill a container having an inlet and an outlet (volume: about 1 ml) to prepare KLRG1-positive cell adsorbers.

<Evaluation of Adsorbability of KLRG1-Positive Cells>

The ACD-A (acid citrate dextrose solution-A)-added human fresh blood (2.0 ml; blood: ACD-A=8:1) was introduced through the inlet into the KLRG1-positive cell adsorber with the use of a syringe pump at a flow rate of 1.0 ml/min, and the treated blood was recovered at the column outlet. The ACD-A-added human fresh blood before introduction into the column and the blood recovered at the column outlet were independently diluted with PBS(−) at 1:1, the resultants were superposed on Ficoll-Paque PLUS (GE Healthcare), and centrifugation was carried out at 400×g for 30 minutes to obtain a mononuclear cell suspension. The KLRG1-positive cells in NK cells in the mononuclear cell suspension were assayed with the use of the anti-human CD3 antibody, the anti-human CD56 antibody, and the anti-human KLRG1 antibody directly or indirectly labeled with fluorescence using FACSCalibur™ (Becton Dickinson). As a result, the adsorption of CD3$^-$CD56$^+$ KLRG1-positive cells in the NK cells (hereafter abbreviated as "KLRG1$^+$ NK cells") was found to be 93.2%. The adsorption of CD3$^-$CD56$^+$KLRG1-negative cells in the NK cells (hereafter abbreviated as "KLRG1$^-$NK cells") was 19.1%, that of lymphocytes was 16.9%, and that of platelets was 15.8%. This indicates that KLRG1$^+$ NK cells were specifically adsorbed (Table 1).

Example 3

The KLRG1-positive cell adsorbing materials were prepared using nonwoven fabric (average fiber diameter: 16.9 μm; fiber weight per unit area: 80 g/m$^2$; thickness: approximately 0.8 mm), and 12 pieces of such nonwoven fabric was used to fill, so as to prepare the KLRG1-positive cell adsorbers. Subsequently, the adsorbability of KLRG1-positive cells was evaluated in the same manner as in Example 2, except that 2.0 ml of the ACD-A-added human fresh blood (blood: ACD-A=8:1) was introduced through the inlet into the KLRG1-positive cell adsorber with the use of a syringe pump at a flow rate of 0.2 ml/min. As a result, the adsorption of the KLRG1$^+$ NK cells was found to be 83.9%. The adsorption of the KLRG1$^-$NK cells was 10.5%, that of lymphocytes was 5.7%, and that of platelets was 7.7%. This indicates that KLRG1$^-$NK cells were specifically adsorbed (Table 1).

Example 4

The KLRG1-positive cell adsorber was prepared in the same manner as in Example 2, except that the KLRG1-positive cell adsorbing materials were prepared with the use of the anti-mouse KLRG1 monoclonal antibody that cross-reacts with human KLRG1. Subsequently, the adsorbability of KLRG1-positive cells was evaluated in the same manner as in Example 2, except that 2.0 ml of the ACD-A-added human fresh blood (blood: ACD-A=8:1) was introduced through the inlet into the KLRG1-positive cell adsorber with the use of a syringe pump at a flow rate of 0.2 ml/min. As a result, the adsorption of the KLRG1$^+$ NK cells was found to be 90.3%. The adsorption of the KLRG1" NK cells was 0.0%, that of lymphocytes was 27.8%, and that of platelets was 0.0%. This indicates that KLRG1$^+$NK cells were specifically adsorbed (Table 1).

Example 5

The KLRG1-positive cell adsorber was prepared in the same manner as in Example 2, except that activated nonwoven fabric on which human E-cadherin (Cat. No: 648-EC, R&D Systems, Inc.) had been immobilized instead of the rabbit anti-human KLRG1 polyclonal antibody was used. Subsequently, the adsorbability of KLRG1-positive cells was evaluated in the same manner as in Example 2, except that 2.0 ml of the ACD-A-added human fresh blood (blood: ACD-A=8:1) was introduced through the inlet into the KLRG1-positive cell adsorber with the use of a syringe pump at a flow rate of 0.2 ml/min. As a result, the adsorption of the KLRG1$^+$ NK cells was found to be 32.7%. The adsorption of the KLRG1$^-$NK cells was 8.8%, that of lymphocytes was 22.2%, and that of platelets was 26.4%. This indicates that KLRG1$^+$ NK cells were specifically adsorbed (Table 1).

TABLE 1

| | Adsorption of KLRG1$^+$NK cells (%) | Adsorption of KLRG1$^-$NK cells (%) | Adsorption of lymphocytes (%) | Adsorption of platelets (%) |
|---|---|---|---|---|
| Example 2 | 93.2 | 19.1 | 16.9 | 15.8 |
| Example 3 | 83.9 | 10.5 | 5.7 | 7.7 |
| Example 4 | 90.3 | 0.0 | 27.8 | 0.0 |
| Example 5 | 32.7 | 8.8 | 22.2 | 26.4 |

Example 6

(A) Method (1) Cell Line

The HER2-positive human gastric cancer cell line (MKN-7) was provided by RIKEN Cell Bank. The HER2-positive human gastric cancer cell line (NCI-N87) was purchased from ATCC. MKN-7 was confirmed to be pan-cadherin-negative and E-cadherin-negative. NCI-N87 was confirmed to be pan-cadherin-positive and E-cadherin-positive. MKN-7 and NCI-N87 were cultured in the same manner as in Example 1, except that fetal bovine serum, penicillin, and streptomycin were added to RPMI-1640 medium (Sigma Aldrich, Mo., U.S.A.).

(B) Results (1) Cytotoxicity of Trastuzumab and Peripheral Blood Mononuclear Cells or Peripheral Blood Mononuclear Cells from which KLRG1-Expressing Cells Had been Removed on MKN-7 Gastric Cancer Cells (FIG. 8)

Figure 8A:
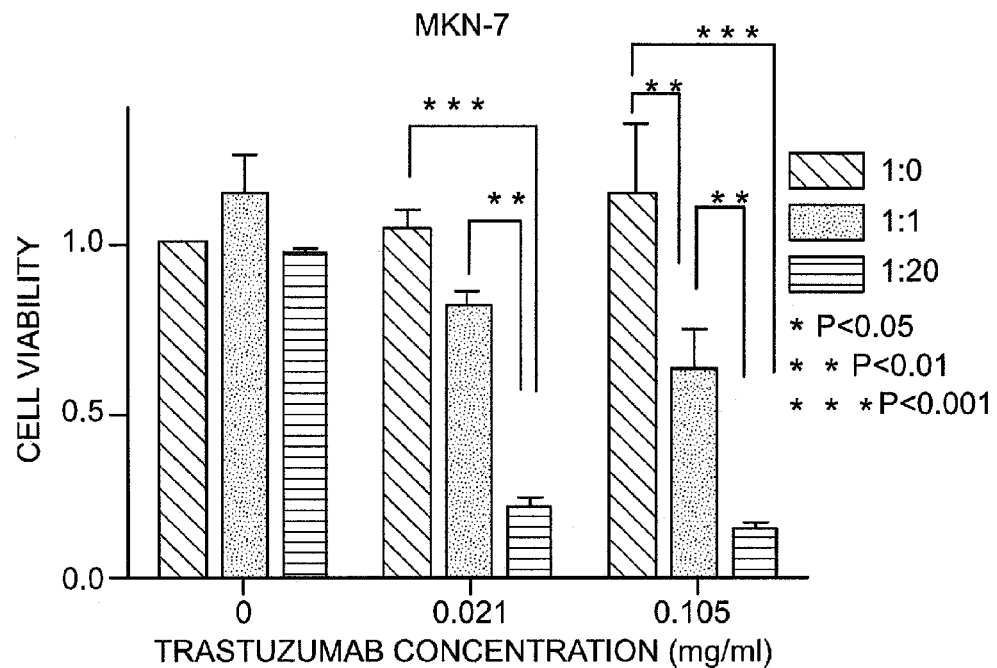
FIG. 8 shows cytotoxicity of trastuzumab and peripheral blood mononuclear cells or peripheral blood mononuclear cells from which KLRG1-expressing cells had been removed on MKN-7 gastric cancer cells. An experiment was carried out in the same manner as in Example 1. The mean and the standard deviation of triplicate assays are shown. Statistical analysis was carried out via two-way ANOVA. (A: peripheral blood mononuclear cells; B: peripheral blood mononuclear cells from which KLRG1-expressing cells were removed)

MKN-7 (pan-cadherin negative) did not exhibit any change in tumor cell viability at a trastuzumab concentration of 0, 0.021 mg/ml, or 0.105 mg/ml, when the peripheral blood mononuclear cells were not cultured together. When the trastuzumab concentration was set at 0, no change was observed in tumor cell viability even when the tumor cells were cultured with the same or 20 times greater the amount of the peripheral blood mononuclear cells. When the trastuzumab concentration was set at 0.021 mg/ml and the tumor cells were cultured with the same amount of peripheral blood mononuclear cells, however, tumor cell viability was likely to be lowered, compared with a case in which the peripheral blood mononuclear cells were not cultured together, although no statistically significant difference was observed. When the tumor cells were cultured with 20 times greater the amount of the peripheral blood mononuclear cells, tumor cell viability was further lowered, and tumor cell viability was significantly lowered, compared with the cases in which the peripheral blood mononuclear cells were not cultured together and in which the tumor cells were cultured with the same amount of the peripheral blood mononuclear cells. When the trastuzumab concentration was set at 0.105 mg/ml and the tumor cells were cultured with the same amount of the peripheral blood mononuclear cells, tumor cell viability was significantly lowered, compared with a case in which the peripheral blood mononuclear cells were not cultured together. When the tumor cells were cultured with 20 times greater the amount of the peripheral blood mononuclear cells, tumor cell viability was further lowered, and tumor cell viability was significantly lowered compared with the cases in which the peripheral blood mononuclear cells were not cultured together and in which the tumor cells were cultured with the same amount of the peripheral blood mononuclear cells. The results demonstrate that tumor cell viability of MKN-7, which would not involve cadherin expression, would be lowered depending on the number of peripheral blood mononuclear cells, regardless of the trastuzumab concentration (FIG. 8A).

A similar experiment was carried out using peripheral blood mononuclear cells from which KLRG1-expressing cells had been removed.

Figure 8B:
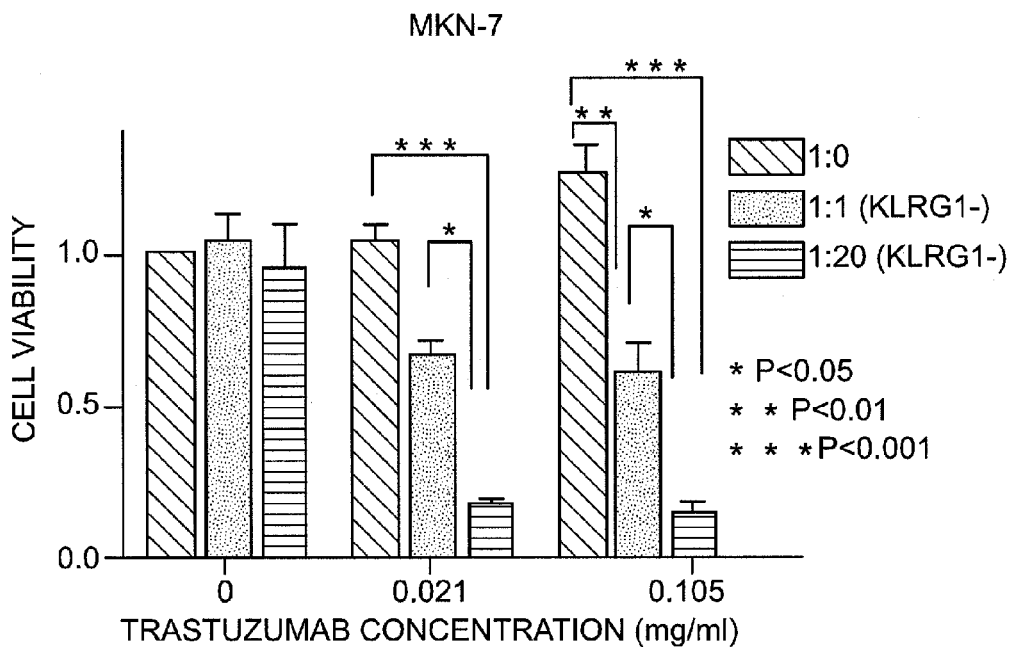

No change was observed in tumor cell viability at a trastuzumab concentration of 0, 0.021 mg/ml, or 0.105 mg/ml when the peripheral blood mononuclear cells were not cultured together. When the trastuzumab concentration was set at 0, no change was observed in tumor cell viability even when the tumor cells were cultured with the same or 20 times greater the amount of the peripheral blood mononuclear cells from which KLRG1-expressing cells had been removed. When the trastuzumab concentration was set at 0.021 mg/ml and the tumor cells were cultured with 20 times greater the amount of the peripheral blood mononuclear cells from which KLRG1-expressing cells had been removed, the number of viable tumor cells decreased, and tumor cell viability was significantly lowered, compared with the cases in which the peripheral blood mononuclear cells were not cultured together and in which the tumor cells were cultured with the same amount of the peripheral blood mononuclear cells from which KLRG1-expressing cells had been removed. When the tumor cells were cultured with the same amount of the peripheral blood mononuclear cells from which KLRG1-expressing cells had been removed, tumor cell viability was likely to be lowered, compared with a case in which the peripheral blood mononuclear cells were not cultured together, although no statistically significant difference was observed. When the trastuzumab concentration was set at 0.105 mg/ml and the tumor cells were cultured with the same amount of the peripheral blood mononuclear cells from which KLRG1-expressing cells had been removed, tumor cell viability was significantly lowered compared with a case in which the peripheral blood mononuclear cells were not cultured together. When the tumor cells were cultured with 20 times greater the amount of the peripheral blood mononuclear cells from which KLRG1-expressing cells had been removed, tumor cell viability was further lowered, and tumor cell viability was significantly lowered compared with the cases in which the peripheral blood mononuclear cells were not cultured together and in which the tumor cells were cultured with the same amount of the peripheral blood mononuclear cells from which KLRG1-expressing cells had been removed. The results demonstrate that tumor cell viability of MKN-7, which would not involve cadherin expression, would be lowered depending on the number of peripheral blood mononuclear cells from which KLRG1-expressing cells had been removed, regardless of the trastuzumab concentration (FIG. 8B).

(2) Cytotoxicity of Trastuzumab and Peripheral Blood Mononuclear Cells or Peripheral Blood Mononuclear Cells from which KLRG1-Expressing Cells Had been Removed on NCI-N87 Gastric Cancer Cells (FIG. 9)

Figure 9A:
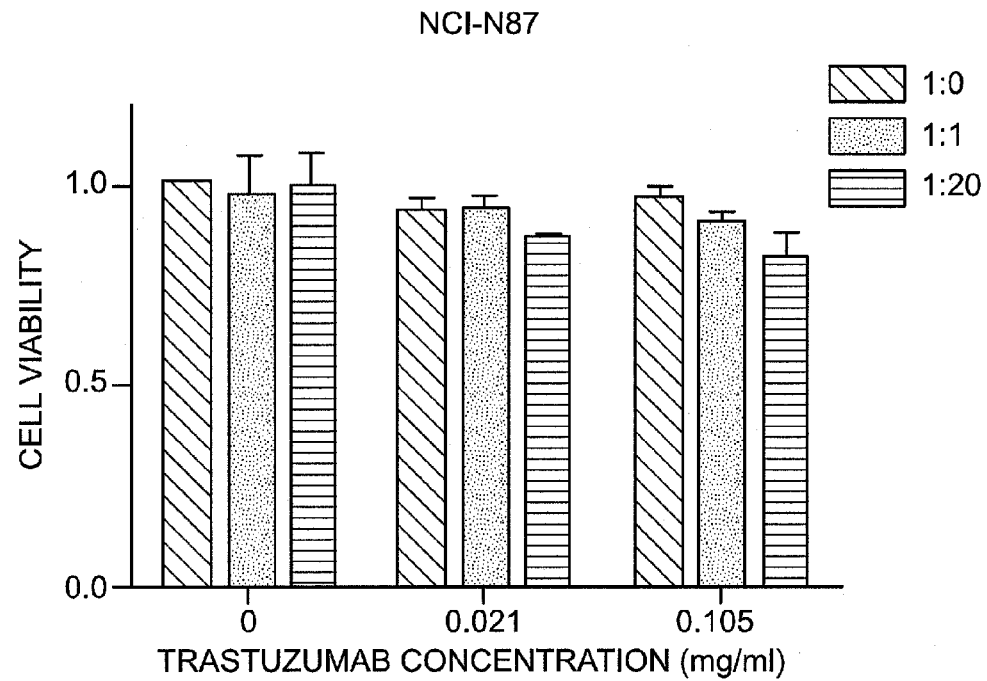
FIG. 9 shows cytotoxicity of trastuzumab and peripheral blood mononuclear cells or peripheral blood mononuclear cells from which KLRG1-expressing cells had been removed on NCI-N87 gastric cancer cells. An experiment was carried out in the same manner as in Example 1. The mean and the standard deviation of triplicate assays are shown. Statistical analysis was carried out via two-way ANOVA. (A: peripheral blood mononuclear cells, B: peripheral blood mononuclear cells from which KLRG1-expressing cells were removed)

NCI-N87 (pan-cadherin positive and E-cadherin positive) did not exhibit any change in tumor cell viability at a trastuzumab concentration of 0, 0.021 mg/ml, or 0.105 mg/ml, when the peripheral blood mononuclear cells were not cultured together. When the trastuzumab concentration was set at 0, no change was observed in tumor cell viability even when the tumor cells were cultured with the same or 20 times greater the amount of the peripheral blood mononuclear cells. When the trastuzumab concentration was set at 0.021 mg/ml and the tumor cells were cultured with the same amount of peripheral blood mononuclear cells, tumor cell viability did not change as in the case in which the peripheral blood mononuclear cells were not cultured together. Also, tumor cell viability did not change when the tumor cells were cultured with 20 times greater the amount of the peripheral blood mononuclear cells. Such tendency was also observed when the trastuzumab concentration was set at 0.105 mg/ml, and no change was observed in tumor cell viability even when the tumor cells were cultured with the same or 20 times greater the amount of the peripheral blood mononuclear cells. The results demonstrate that tumor cell viability of NCI-N87 involving cadherin expression would not be changed, regardless of the trastuzumab concentration and the peripheral blood mononuclear cell count (FIG. 9A).

A similar experiment was carried out using peripheral blood mononuclear cells from which KLRG1-expressing cells had been removed.

Figure 9B:
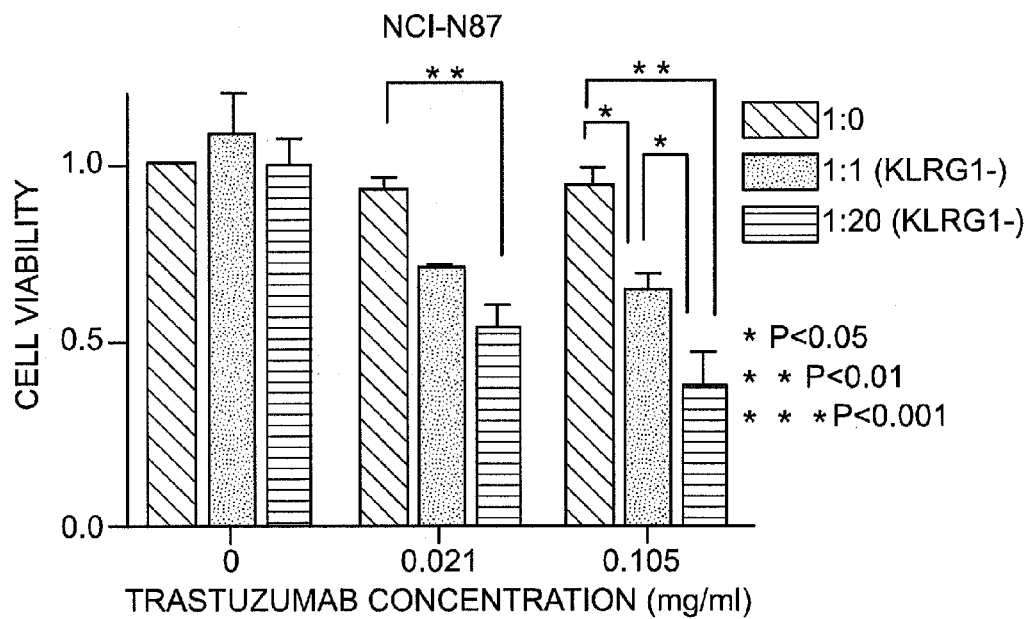

No change was observed in tumor cell viability at a trastuzumab concentration of 0, 0.021 mg/ml, or 0.105 mg/ml, when the peripheral blood mononuclear cells were not cultured together. When the trastuzumab concentration was set at 0, no change was observed in tumor cell viability even when the tumor cells were cultured with the same or 20 times greater the amount of the peripheral blood mononuclear cells from which KLRG1-expressing cells had been removed. When the trastuzumab concentration was set at 0.021 mg/ml and the tumor cells were cultured with the same amount of the peripheral blood mononuclear cells from which KLRG1-expressing cells had been removed, however, tumor cell viability was likely to be lowered, compared with a case in which the peripheral blood mononuclear cells were not cultured together, although no statistically significant difference was observed. When the tumor cells were cultured with 20 times greater the amount of the peripheral blood mononuclear cells from which KLRG1-expressing cells had been removed, tumor cell viability was further lowered, and tumor cell viability was significantly lowered, compared with a case in which the peripheral blood mononuclear cells were not cultured together. When the trastuzumab concentration was set at 0.105 mg/ml and the tumor cells were cultured with the same amount of the peripheral blood mononuclear cells from which KLRG1-expressing cells had been removed, tumor cell viability was significantly lowered, compared with a case in which the peripheral blood mononuclear cells were not cultured together. When the tumor cells were cultured with 20 times greater the amount of the peripheral blood mononuclear cells from which KLRG1-expressing cells had been removed, tumor cell viability was further lowered, and tumor cell viability was significantly lowered compared with cases in which the peripheral blood mononuclear cells were not cultured together and in which the tumor cells were cultured with the same amount of the peripheral blood mononuclear cells from which KLRG1-expressing cells had been removed (FIG. 9B).

(C) Summary

As with the case of the HER2-positive human breast cancer cell line, it was confirmed that the E-cadherin-positive HER2-positive human gastric cancer cell line exhibited resistance to trastuzumab and the E-cadherin-negative HER2-positive human gastric cancer cell line exhibited sensitivity to trastuzumab. Since the existence of peripheral blood mononuclear cells was essential for the expression of trastuzumab sensitivity, involvement of ADCC activity was deduced. By selectively reducing the NK cells that express KLRG1 (i.e., the inhibitory receptor that recognizes E-cadherins in the NK cells as ligands) from the peripheral blood mononuclear cells, trastuzumab resistance of the E-cadherin-positive cell line was found to be quenched.

Example 7

(A) Method (1) Mouse

Female NOD/SCID mice (6-week-old, non-obese diabetic/severe combined immune deficient mice) were purchased from CLEA Japan, Inc. All animals were maintained and handled in accordance with the guidelines of the institution based on approved protocols.

(2) Administration of Trastuzumab and Peripheral Blood Mononuclear Cells

HER2-positive pan-cadherin-positive human breast cancer cells (HCC1569) ($5.0 \times 10^6$ cells) were suspended in 0.2 ml of PBS, and the NOD/SCID mice were inoculated hypodermically with the suspension. These tumor-bearing mice were divided into the following five groups: 1) the control group; 2) the group to which the human peripheral blood mononuclear cells from which KLRG1-expressing cells had been removed were administered; 3) the group to which trastuzumab was administered; 4) the group to which the human peripheral blood mononuclear cells and trastuzumab were administered; and 5) the group to which the human peripheral blood mononuclear cells from which KLRG1-expressing cells had been removed and trastuzumab were administered. Trastuzumab was administered intraperitoneally in an amount of 0.005 mg per g of mouse body weight. Human peripheral blood mononuclear cells were administered intraperitoneally in an amount of $5.0 \times 10^6$ cells per mouse. Administration of trastuzumab and human peripheral blood mononuclear cells was initiated 4 weeks after HCC1569 inoculation, and administration was carried out once a week for 4 weeks.

(3) Measurement of Tumor Volume

The length, width, and thickness of the tumor were measured using calipers once a week, and the tumor volume was calculated by the following equation.

$$\text{Tumor volume (mm}^3\text{)} = (\text{length}) \times (\text{width}) \times (\text{thickness})$$

(B) Results

Figure 10:
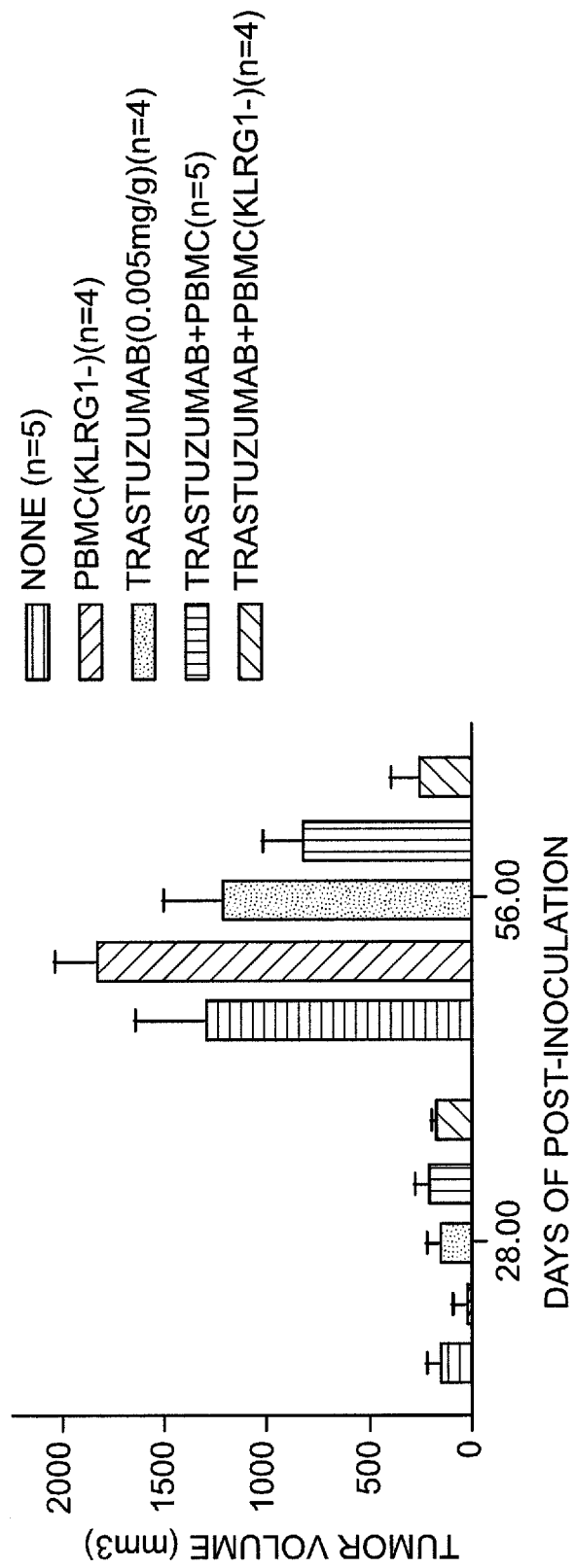
FIG. 10 shows the effects of suppressing the growth of HCC1569 breast cancer cells administered to NOD/SCID mice of trastuzumab and human peripheral blood mononuclear cells from which KLRG1-expressing cells were removed.

FIG. 10 shows the data regarding the tumor volume 28 days (4 weeks) and 56 days (8 weeks) after HCC1569 inoculation. As a result of comparison of the data from 28 days and 56 days after HCC1569 inoculation, tumor volume was found to have increased in the control group, the group to which the human peripheral blood mononuclear cells from which KLRG1-expressing cells had been removed were administered, the group to which trastuzumab was administered, and the group to which the human peripheral blood mononuclear cells and trastuzumab were administered. No increase in tumor volume was observed in the group to which the human peripheral blood mononuclear cells from which KLRG1-expressing cells had been removed and trastuzumab were administered.

Example 8

(A) Method (1) Mouse KLRG1-Positive Cell Adsorbers

The activated nonwoven fabric of Example 2, which had been cut into 6 circular pieces each with a diameter of 0.48 cm, and the anti-mouse KLRG1 monoclonal antibody (eBioscience) were used to prepare mouse KLRG1-positive cell adsorbing materials in accordance with the method of Example 2. Further, the mouse KLRG1-positive cell adsorbing materials were used to fill a container having an inlet and an outlet (volume: about 0.05 ml) in accordance with the method of Example 2 to prepare mouse KLRG1-positive cell adsorber.

(2) Evaluation of Adsorbability of Mouse KLRG1-Positive Cells

The ACD-A (acid citrate dextrose solution-A, Terumo Corporation)-added mouse fresh blood (3.0 ml; blood: ACD-A=8:1) was introduced through the inlet into the mouse KLRG1-positive cell adsorbers with the use of a syringe pump at a flow rate of 0.064 ml/min, and the treated blood was recovered at the outlet of the mouse KLRG1-positive cell adsorbers. The blood samples before and after treatment with the mouse KLRG1-positive cell adsorbers were stained with the fluorescence-labeled anti-mouse CD3 antibody, anti-mouse CD49b antibody, and anti-mouse KLRG1 antibody, and CD3−.CD49b$^+$ cells were analyzed with a flow cytometer (Cytomics FC 500, Beckman Coulter) as the NK cells.

(B) Results

The adsorption of CD3−, CD49b$^+$, and KLRG1$^+$ mouse KLRG1$^+$ NK cells was 98.4%, that of CD3$^-$, CD49b$^+$, and KLRG1$^-$ mouse KLRG1$^-$ NK cells was 45.4%, that of mouse lymphocytes was 26.3%, and that of mouse platelets was −2.5%. This indicates that mouse KLRG1$^+$ cells were specifically adsorbed from the mouse blood (Table 2).

TABLE 2

| | Adsorption of mouse KLRG1$^+$NK cells (%) | Adsorption of mouse KLRG1$^-$NK cells (%) | Adsorption of mouse lymphocytes (%) | Adsorption of mouse platelets (%) |
|---|---|---|---|---|
| Example 8 | 98.4% | 45.4% | 26.3% | −2.3% |

Example 9

(A) Method (1) Design of Apparatus for Mouse Extracorporeal Circulation

The circuits used for mouse extracorporeal circulation were prepared using a silicone tube (inner diameter: 0.5 mm; outer diameter: 4 mm), two urethane tubes (outer diameter: 0.6 mm; inner diameter: 0.3 mm), and mini-fittings (VPY106, ISIS Co., Ltd.) in combination. The internal volume of the circuit was 0.09 ml. A Perista Pump (type SJ-1211H, ATTO) was used as the power source for extracorporeal circulation, and the flow rate was set at 0.064 ml/min. During extracorporeal circulation, ACD-A was continuously administered at 0.008 ml/min with the use of a microsyringe pump from mini-fittings in the circuits. The mouse KLRG1-positive cell adsorbers of Example 8 were connected to the circuits, the solution of ACD-A and physiological saline mixed at 11:14 was introduced thereinto, and priming was then carried out for 15 minutes.

(2) Mouse

Nude mice (BALB/c-nu/nu, 6-week-old, female, Japan SLC, Inc.) were inoculated hypodermically with a suspension of 5.0×10$^6$ HER2-positive pan-cadherin-positive human breast cancer cells (HCC1569) in 0.2 ml of PBS. These tumor bearing mice were divided into the following three groups 4 weeks later: a) the control group; b) the group to which trastuzumab was administered; and c) the group subjected to extracorporeal circulation of the blood in an amount twice the amount of the entire blood and trastuzumab administration. Each group consisted of 6 mice (n=6). Extracorporeal circulation and trastuzumab administration were carried out once a week over a period of 3 weeks, and trastuzumab was administered intraperitoneally in an amount of 0.005 mg per g of mouse body weight. All animals were maintained and handled in accordance with the guidelines of the institution based on approved protocols.

(3) Method of Mouse Extracorporeal Circulation

The tumor bearing mice were subjected to isoflurane anesthesia, and the skin was incised to expose both cervical veins. Surflo F&F (Terumo Corporation) was allowed to indwell in both cervical veins, which were separately designated as a blood removal port and a retransfusion port, and connected to the circuits. With reference to Jikken Doubutsu No Ketsueki-gaku (Haematology of Experimental Animals, Masatoshi Seki et al., Life Science, 1981), the total blood amounts of the mice were calculated, and the blood that was twice the amount of the entire blood was treated via extracorporeal circulation. Thereafter, physiological saline was introduced over a period of 2 minutes and 30 seconds to retransfuse the blood in the mouse KLRG1-positive cell adsorbers and the circuits into the mice. Bleeding was stopped and the wounds were then stitched up.

(4) Measurement of Tumor Volume

Tumor volume was measured in the same manner as in Example 7 (3).

(B) Results

Table 3 shows average values of tumor volumes for each group before treatment and 1 to 3 weeks after treatment and the percentages of increase in tumor volume after treatment relative to that before treatment for n=6 (n=5: group c 3 weeks later).

TABLE 3

| | Tumor volume (mm$^3$) of each group (n = 6) (percentage of changes) | | |
|---|---|---|---|
| Number of days after treatment | a) Control group | b) Group subjected to trastuzumab administration | c) Group in which 200% blood was treated via extracorporeal circulation and to which trastuzumab was administered |
| Before treatment | 149.5 (100%) | 164.1 (100%) | 202.6 (100%) |
| 1 week later | 276.4 (185%) | 238.3 (145%) | 168.8 (83%) |

TABLE 3-continued

Tumor volume (mm³) of each group (n = 6) (percentage of changes)

| Number of days after treatment | a) Control group | b) Group subjected to trastuzumab administration | c) Group in which 200% blood was treated via extracorporeal circulation and to which trastuzumab was administered |
|---|---|---|---|
| 2 week later | 458.6 (307%) | 502.7 (306%) | 286.6 (141%) |
| 3 week later | 919.8 (615%) | 1074.1 (655%) | 357.9 (177%) |

Regarding the control group ((a) in Table 3), the percentage of increase in tumor volume was 185% one week later, 307% two weeks later, and 615% 3 weeks later compared with the tumor volume before treatment. Regarding the group to which trastuzumab was administered ((b) in Table 3), the tumor volume was also likely to increase, the percentage of increase was 145% one week later, 306% two weeks later, and 655% 3 weeks later.

Regarding the group that was subjected to extracorporeal circulation of the blood in an amount twice the amount of the entire blood and trastuzumab administration ((c) in Table 3), the percentage of increase was 83% one week later, 141% two weeks later, and 177% 3 weeks later. The group that was subjected to extracorporeal circulation of the blood in an amount twice the amount of the entire blood and trastuzumab administration ((c) in Table 3) exhibited a tendency of decrease in tumor volume one week later, and tumor increase was suppressed at more significant levels three weeks later, compared with the control group ((a) in Table 3) and the group to which trastuzumab was administered ((b) in Table 3) (p=0.018 and p=0.038, respectively).

As is apparent from the above results of experiment, use of treatment via extracorporeal circulation in combination with antibody drugs yields significant anti-cancer effects on a living individual with epithelial cancer, which is positive for a KLRG1 ligand.

The invention claimed is:

1. A method for treating a living individual with epithelial cancer, the epithelial cancer being positive for a cancer-specific membrane antigen expressed in epithelial cancer cells and positive for a KLRG1 ligand, the method comprising:
   selectively reducing KLRG1-positive immunocytes in the peripheral blood of the living individual with epithelial cancer ex vivo;
   administering to the living individual the peripheral blood from which the KLRG1-positive immunocytes have been selectively reduced, wherein the adsorption percentage of the KLRG1-positive immunocytes (B)/the adsorption percentage of the KLRG1-negative immunocytes (A) is >2; and
   administering to the living individual a therapeutic agent for cancer comprising an antibody reacting with the cancer-specific membrane antigen and having antibody-dependent cell cytotoxicity.

2. The method according to claim 1, wherein the ex vivo selective reduction of KLRG1-positive immunocytes comprises extracorporeally circulating the peripheral blood of a living individual and allowing the same to pass through a cell adsorber having higher affinity for KLRG1-positive immunocytes than for KLRG1-negative immunocytes.

3. The method according to claim 1, wherein administration of a therapeutic agent for cancer is carried out during or after the selective reduction of the KLRG1-positive immunocytes in the peripheral blood of the living individual ex vivo.

4. The method according to claim 1, wherein the method is carried out a plurality of times.

5. The method according to claim 1, wherein the cancer-specific membrane antigen expressed in epithelial cancer cells is HER2.

6. The method according to claim 5, wherein an antibody reacting with the cancer-specific membrane antigen expressed in epithelial cancer cells is trastuzumab.

7. The method according to claim 1, wherein the cancer-specific membrane antigen expressed in epithelial cancer cells is CEA.

8. The method according to claim 1, wherein the KLRG1-positive immunocytes are KLRG1-positive NK cells.

9. The method according to claim 1, wherein the KLRG1 ligand is selected from the group consisting of E-cadherin, N-cadherin, R-cadherin, and a fragment of any thereof.

10. The method according to claim 1, wherein the eptithelial cancer is breast cancer.

11. The method according to claim 1, wherein the eptithelial cancer is gastric cancer.

12. The method according to claim 2, wherein the cell adsorber having higher affinity for KLRG1-positive immunocytes than for KLRG1-negative immunocytes comprises a water-insoluble carrier on which a substance having affinity for KLRG1 is immobilized.

13. The method according to claim 12, wherein the substance having affinity for KLRG1 is an antibody reacting with KLRG1.

14. The method according to claim 12, wherein the substance having affinity for KLRG1 is E-cadherin.

15. The method according to claim 12, wherein the water-insoluble carrier is magnetic particles.

16. The method according to claim 12, wherein the water-insoluble carrier is a nonwoven fabric.

17. A method for treating a living individual with epithelial cancer positive for a cancer-specific membrane antigen and positive for a KLRG1 ligand, the method comprising:
   selectively reducing KLRG1-positive immunocytes in the peripheral blood of a living individual with epithelial cancer ex vivo with the use of a cell adsorber having higher affinity for KLRG1-positive immunocytes than for KLRG1-negative immunocytes, wherein the adsorption percentage of the KLRG1-positive immunocytes (B)/the adsorption percentage of the KLRG1-negative immunocytes (A) is >2; and
   administering, to the living individual, (i) the peripheral blood from which the KLRG1-positive immunocytes have been selectively reduced, and (ii) a therapeutic agent for cancer comprising an antibody reacting with the cancer-specific membrane antigen and having antibody-dependent cell cytotoxicity.

18. The method according to claim 17, wherein the ex vivo selective reduction of KLRG1-positive immunocytes comprises extracorporeally circulating the peripheral blood of a living individual and allowing the same to pass through a cell adsorber having higher affinity for KLRG1-positive immunocytes than for KLRG1-negative immunocytes to selectively reduce KLRG1-positive immunocytes.

19. The method according to claim 17, wherein the KLRG1-positive immunocytes are KLRG1-positive NK cells.

* * * * *